(12) United States Patent
Xu et al.

(10) Patent No.: US 9,969,786 B2
(45) Date of Patent: May 15, 2018

(54) TROPHIC HORMONE FUSION PROTEIN, PREPARATION METHOD AND APPLICATION THEREOF

(71) Applicant: SUZHOU ALPHAMAB CO., LTD., Suzhou, Jiangsu (CN)

(72) Inventors: Ting Xu, Jiangsu (CN); Kangping Guo, Jiangsu (CN); Lihong Yun, Jiangsu (CN)

(73) Assignee: Suzhou Alphamab Co, Ltd., Suzhou Jiangsu (CN)

( * ) Notice: Subject to any disclaimer, the term of this patent is extended or adjusted under 35 U.S.C. 154(b) by 0 days. days.

(21) Appl. No.: 14/646,926

(22) PCT Filed: Nov. 22, 2013

(86) PCT No.: PCT/CN2013/087676
§ 371 (c)(1),
(2) Date: May 22, 2015

(87) PCT Pub. No.: WO2014/079384
PCT Pub. Date: May 30, 2014

(65) Prior Publication Data
US 2016/0060321 A1 Mar. 3, 2016

(30) Foreign Application Priority Data

Nov. 22, 2012 (CN) .......................... 2012 1 0476665

(51) Int. Cl.
| C07K 14/59 | (2006.01) |
| A61K 38/24 | (2006.01) |
| A61K 38/00 | (2006.01) |

(52) U.S. Cl.
CPC .............. *C07K 14/59* (2013.01); *A61K 38/24* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 4,840,896 A | 6/1989 | Reddy et al. |
| 4,923,805 A | 5/1990 | Reddy et al. |
| 5,155,027 A | 10/1992 | Sledziewski et al. |
| 5,156,957 A | 10/1992 | Reddy et al. |
| 5,338,835 A | 8/1994 | Boime |
| 5,428,130 A | 6/1995 | Capon et al. |
| 5,480,981 A | 1/1996 | Goodwin et al. |
| 5,585,345 A | 12/1996 | Boime |
| 5,639,640 A | 6/1997 | Reddy et al. |
| 5,808,029 A | 9/1998 | Brockhaus et al. |
| 7,740,862 B2 | 6/2010 | Muda et al. |
| 2005/0186662 A1 | 8/2005 | Low |

FOREIGN PATENT DOCUMENTS

| CN | 1926237 A | 3/2007 |
| EP | 0211894 A1 | 3/1987 |
| EP | 0322438 A1 | 7/1989 |
| WO | WO-2005073383 A2 | 8/2005 |
| WO | WO-2013010840 A2 | 1/2013 |

OTHER PUBLICATIONS

Low et al., Human Reproduction, 2005; 20: 1805-1813.*
Zhang et al., Human Reproduction, 2016: 31: 169-182.*
Dumont, et al., Monomeric Fc Fusions Impact on Pharmacokinetic and Biological Activity of Protein Therapeutics, Drug Development, BIodrugs 2006, 20(3):151-160.
European Search Report and opinion, dated Mar. 6, 2016 for EP Application No. 13856451.3.

* cited by examiner

*Primary Examiner* — Christina M Borgeest
(74) *Attorney, Agent, or Firm* — Wilson Sonsini Goodrich & Rosati

(57) ABSTRACT

Disclosed herein is a gonadotropin fusion protein or a thyroid stimulating hormone fusion protein, a method for preparing the same and use thereof. β-subunit of the gonadotropin or thyroid stimulating hormone is fused to an Fc fragment directly or indirectly through a linker, and α-subunit binds to the β-subunit via an affinity between the α-subunit and the β-subunit. The fusion protein has a prolonged half-life and less fluctuating activity.

14 Claims, 10 Drawing Sheets

SEQUENCE LISTING

<160> NUMBER OF SEQ ID NOS: 30

<210> SEQ ID NO 1
<211> LENGTH: 116
<212> TYPE: PRT
<213> ORGANISM: Homo sapiens

<400> SEQUENCE: 1

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115
```

<210> SEQ ID NO 2
<211> LENGTH: 24
<212> TYPE: PRT
<213> ORGANISM: Homo sapiens

<400> SEQUENCE: 2

```
Met Asp Tyr Tyr Arg Lys Tyr Ala Ala Ile Phe Leu Val Thr Leu Ser
1               5                   10                  15

Val Phe Leu His Val Leu His Ser
            20
```

<210> SEQ ID NO 3
<211> LENGTH: 351
<212> TYPE: DNA
<213> ORGANISM: Homo sapiens

<400> SEQUENCE: 3

```
atggattact acagaaaata tgcagctatc tttctggtca cattgtcggt gtttctgcat      60
gttctccatt ccgctcctga tgtgcaggat tgcccagaat gcacgctaca ggaaaaccca     120
ttcttctccc agccgggtgc cccaatactt cagtgcatgg gctgctgctt ctctagagca     180
```

-continued

```
tatcccactc cactaaggtc caagaagacg atgttggtcc aaaagaacgt cacctcagag      240
tccacttgct gtgtagctaa atcatataac agggtcacag taatgggggg tttcaaagtg      300
gagaaccaca cggcgtgcca ctgcagtact tgttattatc acaaatctta a               351
```

```
<210> SEQ ID NO 4
<211> LENGTH: 129
<212> TYPE: PRT
<213> ORGANISM: Homo sapiens

<400> SEQUENCE: 4
```

| Met | Lys | Thr | Leu | Gln | Phe | Phe | Leu | Phe | Cys | Cys | Trp | Lys | Ala | Ile |
|---|---|---|---|---|---|---|---|---|---|---|---|---|---|---|
| 1 |  |  |  | 5 |  |  |  |  | 10 |  |  |  |  | 15 |

| Cys | Cys | Asn | Ser | Cys | Glu | Leu | Thr | Asn | Ile | Thr | Ile | Ala | Ile | Glu | Lys |
|---|---|---|---|---|---|---|---|---|---|---|---|---|---|---|---|
|  |  |  | 20 |  |  |  |  | 25 |  |  |  | 30 |  |  |  |

| Glu | Glu | Cys | Arg | Phe | Cys | Ile | Ser | Ile | Asn | Thr | Thr | Trp | Cys | Ala | Gly |
|---|---|---|---|---|---|---|---|---|---|---|---|---|---|---|---|
|  |  |  | 35 |  |  |  |  | 40 |  |  |  | 45 |  |  |  |

| Tyr | Cys | Tyr | Thr | Arg | Asp | Leu | Val | Tyr | Lys | Asp | Pro | Ala | Arg | Pro | Lys |
|---|---|---|---|---|---|---|---|---|---|---|---|---|---|---|---|
|  | 50 |  |  |  |  | 55 |  |  |  |  | 60 |  |  |  |  |

| Ile | Gln | Lys | Thr | Cys | Thr | Phe | Lys | Glu | Leu | Val | Tyr | Glu | Thr | Val | Arg |
|---|---|---|---|---|---|---|---|---|---|---|---|---|---|---|---|
| 65 |  |  |  |  | 70 |  |  |  |  | 75 |  |  |  |  | 80 |

| Val | Pro | Gly | Cys | Ala | His | His | Ala | Asp | Ser | Leu | Tyr | Thr | Tyr | Pro | Val |
|---|---|---|---|---|---|---|---|---|---|---|---|---|---|---|---|
|  |  |  |  | 85 |  |  |  |  | 90 |  |  |  |  | 95 |  |

| Ala | Thr | Gln | Cys | His | Cys | Gly | Lys | Cys | Asp | Ser | Asp | Ser | Thr | Asp | Cys |
|---|---|---|---|---|---|---|---|---|---|---|---|---|---|---|---|
|  |  |  | 100 |  |  |  |  | 105 |  |  |  | 110 |  |  |  |

| Thr | Val | Arg | Gly | Leu | Gly | Pro | Ser | Tyr | Cys | Ser | Phe | Gly | Glu | Met | Lys |
|---|---|---|---|---|---|---|---|---|---|---|---|---|---|---|---|
|  |  | 115 |  |  |  |  | 120 |  |  |  |  | 125 |  |  |  |

Glu

```
<210> SEQ ID NO 5
<211> LENGTH: 18
<212> TYPE: PRT
<213> ORGANISM: Homo sapiens

<400> SEQUENCE: 5
```

| Met | Lys | Thr | Leu | Gln | Phe | Phe | Leu | Phe | Cys | Cys | Trp | Lys | Ala | Ile |
|---|---|---|---|---|---|---|---|---|---|---|---|---|---|---|
| 1 |  |  |  | 5 |  |  |  |  | 10 |  |  |  |  | 15 |

Cys Cys

```
<210> SEQ ID NO 6
<211> LENGTH: 387
<212> TYPE: DNA
<213> ORGANISM: Homo sapiens

<400> SEQUENCE: 6
atgaagacac tccagttttt cttccttttc tgttgctgga aagcaatctg ctgcaatagc      60
tgtgagctga ccaacatcac cattgcaata gagaaagaag aatgtcgttt ctgcataagc     120
atcaacacca cttggtgtgc tggctactgc tacaccaggg atctggtgta taaggaccca     180
gccaggccca aaatccagaa acatgtacct tcaaggaac tggtatacga aacagtgaga      240
gtgcccggct gtgctcacca tgcagattcc ttgtatacat acccagtggc cacccagtgt     300
cactgtggca gtgtgacag cgacagcact gattgtactg tgcgaggcct ggggcccagc      360
tactgctcct ttggtgaaat gaaagaa                                         387
```

```
<210> SEQ ID NO 7
<211> LENGTH: 227
<212> TYPE: PRT
```

<213> ORGANISM: Homo sapiens

<400> SEQUENCE: 7

```
Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225
```

<210> SEQ ID NO 8
<211> LENGTH: 681
<212> TYPE: DNA
<213> ORGANISM: Homo sapiens

<400> SEQUENCE: 8

```
gacaaaactc acacatgccc accgtgccca gctccggaac tcctgggcgg accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc cccatcgaga aaaccatctc caaagccaaa   360
gggcagcccc gagaaccaca ggtgtacacc ctgcccccat cccgggatga gctgaccaag   420
aaccaggtca gcctgacctg cctggtcaaa ggcttctatc ccagcgacat cgccgtggag   480
tgggagagca atgggcagcc ggagaacaac tacaagacca cgcctcccgt gttggactcc   540
gacggctcct tcttcctcta cagcaagctc accgtggaca agagcaggtg gcagcagggg   600
aacgtcttct catgctccgt gatgcatgag gctctgcaca accactacac gcagaagagc   660
```
ctctccctgt ctccgggtaa a                                                681

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Asn Phe Thr
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Asn Arg Thr
1

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Asn Ile Thr Val Asn Ile Thr Val
1               5

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Glu Thr Asp Thr Leu Ile Leu Trp Arg Leu Leu Leu Trp Val Pro
1               5                   10                  15

Gly Ser Thr Leu Gly Ser Ala
            20

<210> SEQ ID NO 13
<211> LENGTH: 120
<212> TYPE: PRT
<213> ORGANISM: Unknown
<220> FEATURE:
<223> OTHER INFORMATION: Description of Unknown:
      Ursidae family

<400> SEQUENCE: 13

Met Asp Tyr Tyr Arg Lys Tyr Ala Ala Val Ile Leu Thr Thr Leu Ser
1               5                   10                  15

Val Phe Leu His Ile Leu His Ser Phe Pro Asp Gly Glu Phe Thr Met
            20                  25                  30

Gln Gly Cys Pro Glu Cys Lys Leu Lys Glu Asn Lys Tyr Phe Ser Lys

```
              35                   40                  45
Leu Gly Ala Pro Ile Tyr Gln Cys Met Gly Cys Cys Phe Ser Arg Ala
         50                  55                  60
Tyr Pro Thr Pro Ala Arg Ser Lys Lys Thr Met Leu Val Pro Lys Asn
 65                  70                  75                  80
Ile Thr Leu Glu Ala Thr Cys Cys Val Ala Lys Ala Phe Thr Lys Ala
                 85                  90                  95
Thr Val Met Gly Asn Thr Lys Val Glu Asn His Thr Asp Cys His Cys
                100                 105                 110
Ser Thr Cys Tyr Tyr His Lys Ser
                115                 120

<210> SEQ ID NO 14
<211> LENGTH: 120
<212> TYPE: PRT
<213> ORGANISM: Sus scrofa

<400> SEQUENCE: 14

Met Asp Tyr Tyr Arg Lys Tyr Ala Ala Val Ile Leu Ala Ile Leu Ser
 1               5                  10                  15
Val Phe Leu Gln Ile Leu His Ser Phe Pro Asp Gly Glu Phe Thr Met
                20                  25                  30
Gln Gly Cys Pro Glu Cys Lys Leu Lys Glu Asn Lys Tyr Phe Ser Lys
             35                  40                  45
Leu Gly Ala Pro Ile Tyr Gln Cys Met Gly Cys Cys Phe Ser Arg Ala
         50                  55                  60
Tyr Pro Thr Pro Ala Arg Ser Lys Lys Thr Met Leu Val Pro Lys Asn
 65                  70                  75                  80
Ile Thr Ser Glu Ala Thr Cys Cys Val Ala Lys Ala Phe Thr Lys Ala
                 85                  90                  95
Thr Val Met Gly Asn Ala Arg Val Glu Asn His Thr Glu Cys His Cys
                100                 105                 110
Ser Thr Cys Tyr Tyr His Lys Ser
                115                 120

<210> SEQ ID NO 15
<211> LENGTH: 120
<212> TYPE: PRT
<213> ORGANISM: Ovis aries

<400> SEQUENCE: 15

Met Asp Tyr Tyr Arg Lys Tyr Ala Ala Ala Ile Leu Ala Ile Leu Ser
 1               5                  10                  15
Leu Phe Leu Gln Ile Leu His Ser Phe Pro Asp Gly Glu Phe Thr Met
                20                  25                  30
Gln Gly Cys Pro Glu Cys Lys Leu Lys Glu Asn Lys Tyr Phe Ser Lys
             35                  40                  45
Pro Asp Ala Pro Ile Tyr Gln Cys Met Gly Cys Cys Phe Ser Arg Ala
         50                  55                  60
Tyr Pro Thr Pro Ala Arg Ser Lys Lys Thr Met Leu Val Pro Lys Asn
 65                  70                  75                  80
Ile Thr Ser Glu Ala Thr Cys Cys Val Ala Lys Ala Phe Thr Lys Ala
                 85                  90                  95
Thr Val Met Gly Asn Val Arg Val Glu Asn His Thr Glu Cys His Cys
                100                 105                 110
Ser Thr Cys Tyr Tyr His Lys Ser
```

-continued

```
                115                 120

<210> SEQ ID NO 16
<211> LENGTH: 120
<212> TYPE: PRT
<213> ORGANISM: Bos taurus

<400> SEQUENCE: 16

Met Asp Tyr Tyr Arg Lys Tyr Ala Ala Val Ile Leu Thr Ile Leu Ser
1               5                   10                  15

Leu Phe Leu Gln Ile Leu His Ser Phe Pro Asp Gly Glu Phe Thr Met
            20                  25                  30

Gln Gly Cys Pro Glu Cys Lys Leu Lys Glu Asn Lys Tyr Phe Ser Lys
        35                  40                  45

Pro Asp Ala Ala Ile Tyr Gln Cys Met Gly Cys Cys Phe Ser Arg Ala
    50                  55                  60

Tyr Pro Thr Pro Ala Arg Ser Lys Lys Thr Met Leu Val Pro Lys Asn
65                  70                  75                  80

Ile Thr Ser Glu Ala Thr Cys Cys Val Ala Lys Ala Phe Thr Lys Ala
                85                  90                  95

Thr Val Met Gly Asn Val Arg Val Glu Asn His Thr Gly Cys His Cys
            100                 105                 110

Ser Thr Cys Tyr Tyr His Lys Ser
        115                 120

<210> SEQ ID NO 17
<211> LENGTH: 116
<212> TYPE: PRT
<213> ORGANISM: Homo sapiens

<400> SEQUENCE: 17

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
    115

<210> SEQ ID NO 18
<211> LENGTH: 120
<212> TYPE: PRT
<213> ORGANISM: Rattus norvegicus

<400> SEQUENCE: 18

Met Asp Cys Tyr Arg Arg Tyr Ala Ala Val Ile Leu Val Met Leu Ser
1               5                   10                  15

Met Val Leu His Ile Leu His Ser Leu Pro Asp Gly Asp Leu Ile Ile
            20                  25                  30
```

```
Gln Gly Cys Pro Glu Cys Lys Leu Lys Glu Asn Lys Tyr Phe Ser Lys
            35                  40                  45

Leu Gly Ala Pro Ile Tyr Gln Cys Met Gly Cys Cys Phe Ser Arg Ala
    50                  55                  60

Tyr Pro Thr Pro Ala Arg Ser Lys Lys Thr Met Leu Val Pro Lys Asn
65                  70                  75                  80

Ile Thr Ser Glu Ala Thr Cys Cys Val Ala Lys Ser Phe Thr Lys Ala
                85                  90                  95

Thr Val Met Gly Asn Ala Arg Val Glu Asn His Thr Asp Cys His Cys
            100                 105                 110

Ser Thr Cys Tyr Tyr His Lys Ser
        115                 120

<210> SEQ ID NO 19
<211> LENGTH: 120
<212> TYPE: PRT
<213> ORGANISM: Mus musculus

<400> SEQUENCE: 19

Met Asp Tyr Tyr Arg Lys Tyr Ala Ala Val Ile Leu Val Met Leu Ser
1               5                   10                  15

Met Phe Leu His Ile Leu His Ser Leu Pro Asp Gly Asp Phe Ile Ile
            20                  25                  30

Gln Gly Cys Pro Glu Cys Lys Leu Lys Glu Asn Lys Tyr Phe Ser Lys
            35                  40                  45

Leu Gly Ala Pro Ile Tyr Gln Cys Met Gly Cys Cys Phe Ser Arg Ala
    50                  55                  60

Tyr Pro Thr Pro Ala Arg Ser Lys Lys Thr Met Leu Val Pro Lys Asn
65                  70                  75                  80

Ile Thr Ser Glu Ala Thr Cys Cys Val Ala Lys Ala Phe Thr Lys Ala
                85                  90                  95

Thr Val Met Gly Asn Ala Arg Val Glu Asn His Thr Glu Cys His Cys
            100                 105                 110

Ser Thr Cys Tyr Tyr His Lys Ser
        115                 120

<210> SEQ ID NO 20
<211> LENGTH: 129
<212> TYPE: PRT
<213> ORGANISM: Unknown
<220> FEATURE:
<223> OTHER INFORMATION: Description of Unknown:
      Ursidae family

<400> SEQUENCE: 20

Met Lys Ser Val Gln Leu Cys Phe Leu Phe Cys Cys Trp Arg Ala Ile
1               5                   10                  15

Cys Cys Lys Ser Cys Glu Leu Thr Asn Ile Thr Ile Thr Val Glu Lys
            20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Asn
    50                  55                  60

Ile Gln Lys Ile Cys Thr Phe Lys Glu Leu Ala Tyr Glu Thr Val Lys
65                  70                  75                  80

Val Pro Gly Cys Ala His Gln Ala Asp Ser Leu Tyr Thr Tyr Pro Val
                85                  90                  95
```

```
Ala Thr Glu Cys His Cys Gly Lys Cys Asp Ser Asp Ser Thr Asp Cys
            100                 105                 110

Thr Val Arg Gly Leu Gly Pro Ser Tyr Cys Ser Phe Asn Glu Met Lys
        115                 120                 125

Glu

<210> SEQ ID NO 21
<211> LENGTH: 129
<212> TYPE: PRT
<213> ORGANISM: Sus scrofa

<400> SEQUENCE: 21

Met Lys Ser Leu Gln Phe Cys Phe Leu Phe Cys Cys Trp Lys Ala Ile
1               5                   10                  15

Cys Cys Asn Ser Cys Glu Leu Thr Asn Ile Thr Ile Thr Val Glu Lys
            20                  25                  30

Glu Glu Cys Asn Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Asn
        50                  55                  60

Ile Gln Lys Thr Cys Thr Phe Lys Glu Leu Val Tyr Glu Thr Val Lys
65                  70                  75                  80

Val Pro Gly Cys Ala His His Ala Asp Ser Leu Tyr Thr Tyr Pro Val
                85                  90                  95

Ala Thr Glu Cys His Cys Gly Lys Cys Asp Ser Asp Ser Thr Asp Cys
            100                 105                 110

Thr Val Arg Gly Leu Gly Pro Ser Tyr Cys Ser Phe Ser Glu Met Lys
        115                 120                 125

Glu

<210> SEQ ID NO 22
<211> LENGTH: 129
<212> TYPE: PRT
<213> ORGANISM: Bos taurus

<400> SEQUENCE: 22

Met Lys Ser Val Gln Phe Cys Phe Leu Phe Cys Cys Trp Arg Ala Ile
1               5                   10                  15

Cys Cys Arg Ser Cys Glu Leu Thr Asn Ile Thr Ile Thr Val Glu Lys
            20                  25                  30

Glu Glu Cys Gly Phe Cys Ile Ser Ile Asn Thr Thr Trp Cys Ala Gly
            35                  40                  45

Tyr Cys Tyr Thr Arg Asp Leu Val Tyr Arg Asp Pro Ala Arg Pro Asn
        50                  55                  60

Ile Gln Lys Thr Cys Thr Phe Lys Glu Leu Val Tyr Glu Thr Val Lys
65                  70                  75                  80

Val Pro Gly Cys Ala His His Ala Asp Ser Leu Tyr Thr Tyr Pro Val
                85                  90                  95

Ala Thr Glu Cys His Cys Ser Lys Cys Asp Ser Asp Ser Thr Asp Cys
            100                 105                 110

Thr Val Arg Gly Leu Gly Pro Ser Tyr Cys Ser Phe Arg Glu Ile Lys
        115                 120                 125

Glu

<210> SEQ ID NO 23
```

<211> LENGTH: 129
<212> TYPE: PRT
<213> ORGANISM: Ovis aries

<400> SEQUENCE: 23

Met Lys Ser Val Gln Phe Cys Phe Leu Phe Cys Cys Trp Arg Ala Ile
1               5                   10                  15

Cys Cys Arg Ser Cys Glu Leu Thr Asn Ile Thr Ile Thr Val Glu Lys
            20                  25                  30

Glu Glu Cys Ser Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Asn
    50                  55                  60

Ile Gln Lys Ala Cys Thr Phe Lys Glu Leu Val Tyr Glu Thr Val Lys
65                  70                  75                  80

Val Pro Gly Cys Ala His His Ala Asp Ser Leu Tyr Thr Tyr Pro Val
                85                  90                  95

Ala Thr Glu Cys His Cys Gly Lys Cys Asp Arg Asp Ser Thr Asp Cys
            100                 105                 110

Thr Val Arg Gly Leu Gly Pro Ser Tyr Cys Ser Phe Ser Asp Ile Arg
        115                 120                 125

Glu

<210> SEQ ID NO 24
<211> LENGTH: 129
<212> TYPE: PRT
<213> ORGANISM: Homo sapiens

<400> SEQUENCE: 24

Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu

<210> SEQ ID NO 25
<211> LENGTH: 129
<212> TYPE: PRT
<213> ORGANISM: Rattus norvegicus

<400> SEQUENCE: 25

Met Lys Ser Ile Gln Leu Cys Ile Leu Leu Trp Cys Leu Arg Ala Val
1               5                   10                  15

Cys Cys His Ser Cys Glu Leu Thr Asn Ile Thr Ile Ser Val Glu Lys
            20                  25                  30

```
Glu Glu Cys Arg Phe Cys Ile Ser Ile Asn Thr Thr Trp Cys Glu Gly
            35                  40                  45

Tyr Cys Tyr Thr Arg Asp Leu Val Tyr Lys Asp Pro Ala Arg Pro Asn
 50                  55                  60

Thr Gln Lys Val Cys Thr Phe Lys Glu Leu Val Tyr Glu Thr Ile Arg
65                  70                  75                  80

Leu Pro Gly Cys Ala Arg His Ser Asp Ser Leu Tyr Thr Tyr Pro Val
                85                  90                  95

Ala Thr Glu Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
            115                 120                 125

Glu

<210> SEQ ID NO 26
<211> LENGTH: 129
<212> TYPE: PRT
<213> ORGANISM: Mus musculus

<400> SEQUENCE: 26

Met Lys Leu Ile Gln Leu Cys Ile Leu Phe Trp Cys Trp Arg Ala Ile
1               5                   10                  15

Cys Cys His Ser Cys Glu Leu Thr Asn Ile Thr Ile Ser Val Glu Lys
                20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Asn
 50                  55                  60

Thr Gln Lys Val Cys Thr Phe Lys Glu Leu Val Tyr Glu Thr Val Arg
65                  70                  75                  80

Leu Pro Gly Cys Ala Arg His Ser Asp Ser Leu Tyr Thr Tyr Pro Val
                85                  90                  95

Ala Thr Glu Cys His Cys Gly Lys Cys Asp Ser Asp Ser Thr Asp Cys
                100                 105                 110

Thr Val Arg Gly Leu Gly Pro Ser Tyr Cys Ser Phe Ser Glu Met Lys
            115                 120                 125

Glu

<210> SEQ ID NO 27
<211> LENGTH: 111
<212> TYPE: PRT
<213> ORGANISM: Homo sapiens

<400> SEQUENCE: 27

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
 50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
```

85                  90                  95

Arg Gly Leu Gly Pro Ser Tyr Cys Ser Phe Gly Glu Met Lys Glu
                100                 105                 110

<210> SEQ ID NO 28
<211> LENGTH: 145
<212> TYPE: PRT
<213> ORGANISM: Homo sapiens

<400> SEQUENCE: 28

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
                20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
        50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
                100                 105                 110

Pro Arg Phe Gln Asp Ser Ser Ser Lys Ala Pro Pro Pro Ser Leu
            115                 120                 125

Pro Ser Pro Ser Arg Leu Pro Gly Pro Ser Asp Thr Pro Ile Leu Pro
        130                 135                 140

Gln
145

<210> SEQ ID NO 29
<211> LENGTH: 121
<212> TYPE: PRT
<213> ORGANISM: Homo sapiens

<400> SEQUENCE: 29

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
                20                  25                  30

Ile Cys Ala Gly Tyr Cys Pro Thr Met Met Arg Val Leu Gln Ala Val
            35                  40                  45

Leu Pro Pro Leu Pro Gln Val Val Cys Thr Tyr Arg Asp Val Arg Phe
        50                  55                  60

Glu Ser Ile Arg Leu Pro Gly Cys Pro Arg Gly Val Asp Pro Val Val
65                  70                  75                  80

Ser Phe Pro Val Ala Leu Ser Cys Arg Cys Gly Pro Cys Arg Arg Ser
                85                  90                  95

Thr Ser Asp Cys Gly Gly Pro Lys Asp His Pro Leu Thr Cys Asp His
                100                 105                 110

Pro Gln Leu Ser Gly Leu Leu Phe Leu
            115                 120

<210> SEQ ID NO 30
<211> LENGTH: 118
<212> TYPE: PRT

```
<213> ORGANISM: Homo sapiens

<400> SEQUENCE: 30

Phe Cys Ile Pro Thr Glu Tyr Thr Met His Ile Glu Arg Arg Glu Cys
1               5                   10                  15

Ala Tyr Cys Leu Thr Ile Asn Thr Thr Ile Cys Ala Gly Tyr Cys Met
            20                  25                  30

Thr Arg Asp Ile Asn Gly Lys Leu Phe Leu Pro Lys Tyr Ala Leu Ser
        35                  40                  45

Gln Asp Val Cys Thr Tyr Arg Asp Phe Ile Tyr Arg Thr Val Glu Ile
    50                  55                  60

Pro Gly Cys Pro Leu His Val Ala Pro Tyr Phe Ser Tyr Pro Val Ala
65                  70                  75                  80

Leu Ser Cys Lys Cys Gly Lys Cys Asn Thr Asp Tyr Ser Asp Cys Ile
                85                  90                  95

His Glu Ala Ile Lys Thr Asn Tyr Cys Thr Lys Pro Gln Lys Ser Tyr
                100                 105                 110

Leu Val Gly Phe Ser Val
            115
```

TROPHIC HORMONE FUSION PROTEIN, PREPARATION METHOD AND APPLICATION THEREOF

SEQUENCE LISTING

The instant application contains a Sequence Listing which has been submitted electronically in ASCII format and is hereby incorporated by reference in its entirety. Said ASCII copy, created on Mar. 23, 2017, is named 48344-701_831_SL.txt and is 28,522 bytes in size.

FIELD OF THE INVENTION

The present disclosure relates to a fusion protein. More specifically, the present disclosure relates to a trophic hormone fusion protein, a method for preparing the same and use thereof.

BACKGROUND OF THE INVENTION

Trophic hormones include thyroid stimulating hormone (TSH), adrenocorticotropic hormone and gonadotropins. Gonadotropins are a kind of glycoprotein hormones that regulate gonadal development of vertebrates and promote the production and secretion of gonadal hormones. For example, the luteotropic hormone (LH) and follicle stimulating hormone (FSH) secreted by the anterior pituitary can function synergistically to stimulate the development of ovarian or testicular germ cells, and the production and secretion of gonadal hormones; and human chorionic gonadotropin (HCG) secreted by human placenta can stimulate the secretion of progesterone from the corpus luteum during pregnancy.

Gonadotropins (e.g., LH, FSH, and HCG) and thyroid stimulating hormones collectively constitute a glycoprotein family, and each of them consists of a α-subunit and a β-subunit, wherein the α-subunits are identical among the hormones, while the β-subunits have characteristics specific for each hormone and therefore determine the biological activities and immuno reactivities of the hormones.

Clinically, FSH is useful in assisted reproductive techniques, such as in vitro fertilization (IVF), gamete intra-fallopian transfer (GIFT) and zygote intra-fallopian transfer (ZIFT), to induce superovulation in patients. In addition, it can also be used for females suffering from an ovulia, including patients with polycystic ovarian syndrome not responsive to clomiphene, as well as for males with pituitary gland hypogonadism. LH is usually used in adjunctive treatments with FSH. hCG is mainly used for promoting ovulation and development of the corpus luteum. For males, it can be used to stimulate Leydig cells to secrete testosterone, to test the functions of Leydig cells, and to promote spermatogenesis when used in combination with agonadotropin in a long-term. TSH is usually used in combination with $I^{131}$ for inhibiting and ablating the postoperative residual cancer tissue in patients with thyroid cancer.

Generally, long-term treatment is required in order to achieve a therapeutic effect. However, the dosing regimen of daily intramuscular or subcutaneous injection usually results in local reaction and discomfort. Therefore, it would be useful for practical clinical application to develop a long-acting gonadotropin and thyroid stimulating hormone and to reduce the frequency of administration.

For example, FSH can be isolated from the pituitary gland or the urine of postmenopausal women (see, EP322,438), and can also be produced recombinantly(see, U.S. Pat. Nos. 5,639,640, 5,156,957, 4,923,805, 4,840,896, and EP211, 894). In order to achieve a therapeutic effect, it takes 8-10 consecutive days, sometimes up to 21 days, to stimulate folliculogenesis in females; and it takes up to 18 months to induce spermatogenesis in males with low gonadotropin level. In recent years, a number of patents and publications reported the development of long-acting FSH, the basic strategy of which is to increase the half-life by increasing glycosylation sites in FSH. One way is to increase the glycosylation modification sites within the FSH molecule. WO01/58493 discloses 77 mutations which can be made in the α-subunit of FSH and 51 mutations that can be made in the β-subunit of FSH. However, this patent does not disclose production or measurement of any FSH α- or β-subunit, into which a glycosylation site(s) is introduced by site-directed mutagenesis. U.S. Pat No. 7,740,862 discloses insertion of the GNFT (SEQ ID NO: 9 or GNRT (SEQ ID NO: 10) sequence between amino acid residue 3 and 4 of the α-subunit of FSH, which results in an in vivo half-life of about 17 h in rats, and an ability to in vitro stimulate CHO cells expressing FSH receptors recombinantly to produce cyclic adenosine monophosphate (cAMP) in a manner comparable to that of the native FSH. Another way is to increase glycosylation modification sites by adding additional sequences to the end of the sequence. One of the relatively successful products developed so far is Elonva, which was marketed by Merck, Germany in 2010. This analog has the comparable biological activity as natural FSH but a longer circulation half-life, which is about 69 h in human. The specific protein sequence is disclosed in U.S. Pat. Nos.5, 338,835 and 5,585,345.It contains a modified FSH β-subunit; the C-terminal glutamate of which is extended with the carboxy terminal peptide (CTP) group of hCG. The experimental results of Pieter Verbost, et al. showed that this analog had an in vivo half-life of 17.3 h and 46.9 h in rats and dogs, respectively, which was increased by 1.5-2 olds as compared to that of the recombinant FSH. Signe Perlman, et al. reported a modified FSHα-subunit, with the amino acid sequence "ANITVNITV" (SEQ ID NO: 11) added to the N-terminal. This analogue had an in vivo half-life of 22 h in rats, which was increased by 3-4 folds as compared to that of the recombinant FSH.

IgG immunoglobulin is one of the most abundant proteins in human blood, with a half-life of up to 21 days. Its stability is due to the fact that the Fc fragment of IgG can bind to the neonatal Fc receptor (FcRn), thereby preventing IgG from entering into and being degraded by lysosomes (5-7). Thus, the Fc fragment of IgG is used to link to an active protein to form a fusion protein, thereby increasing the in vivo half-life of the active protein and therefore achieving a long-acting effect. Based on the length of the hinge regions and different amino acid sequences of the Fc fragments, human IgG can be divided into 4 subtypes, among which IgG Fcγ2 has a relatively weak effect of inducing cytotoxicity, and IgG Fcγ1 has the strongest effect. IgG fusion proteins are mostly constructed by linking the N-terminal of the Fc (Hinge-CH2-CH3) fragment or CH (CH1-Hinge-CH2-CH3) fragment of IgG to the C-terminal of an active protein, in order to avoid possible influence of the construction of the fusion protein on the biological activity of the active protein. Furthermore, IgG fusion proteins can be purified efficiently and conveniently by Protein A affinity chromatography. Accordingly, a number of patents have reported that fusion of the Fc fragment of IgG to other proteins can significantly prolong the half-life and increase the in vivo biological activity of the target protein (U.S. Pat. Nos. 5,155,027, 5,428,130, 5,480,981 and 5,808,029).

US patent No. 20050,186,662 discloses that by constructing FSH-Fc fusion protein homodimers and heterodimers, the in vivo half-life in rats was increased to 60 h. As disclosed in the patent, to evaluate the bioactivity of their FSH-Fc fusions, the ovarian weight of rats was measured 72 hours after a single dose of the FSH-Fc fusions or recombinant FSH. The results showed that the ovarian weight in the FSH-Fc fusion protein group (26.9 mg) was increased as compared to the recombinant FSH group (14.3 mg)(the negative control: 12.1 mg). However, due to the sort half-life of the recombinant FSH, daily dosing is usually required in such an activity assay. If administered once every three days according to the protocol, FSH would be substantially metabolized, without any activity. Thus, while ensuring the half-life of the constructed FSH-Fc fusion protein, the activity still remains to be improved.

Therefore, there is a medical need for a product providing full therapeutic effects of gonadotropins or thyroid stimulating hormone, which can be administered less frequently than existing gonadotropin or thyroid stimulating hormone products. In addition, the long acting product can provide a more consistent activity as compared to the activity of gonadotropins or thyroid stimulating hormone achievable by the existing therapies.

SUMMARY OF THE INVENTION

Through persistent efforts, the inventors of the present disclosure discovered unexpectedly that a fusion protein obtained by fusing a β-subunit of a gonadotropin or thyroid stimulating hormone to an Fc fragment of an antibody and binding of the α-subunit to the β-subunit via intermolecular interaction between them, has a longer half-life while maintaining the activity, leading to the present invention.

The first aspect of the present disclosure relates to a fusion protein comprising a trophic hormone protein and an Fc fragment of an antibody, wherein the β-subunit of the trophic hormone protein is linked to the Fc fragment directly or indirectly via a linker, and the α-subunit of the trophic hormone protein binds to the β-subunit via intermolecular interactions between them, and wherein the trophic hormone is selected from the group consisting of luteotropic hormone, follicle stimulating hormone, chorionic gonadotropin and thyroid stimulating hormone, preferably follicle stimulating hormone.

Optionally, the fusion protein further comprises an additional active protein or a tag to facilitate protein purification, e.g., an FLAG tag, a histidine tag, a GST label, a maltose-binding protein tag or the like.

In the present disclosure, the additional active protein or the tag to facilitate protein purification is attached to the N- or C-terminal of the fusion protein.

In one embodiment of the present disclosure, the fusion protein is formed by fusion of the trophic hormone protein to the Fc fragment of an antibody.

In one embodiment of the present disclosure, the trophic hormone is a follicle stimulating hormone (FSH).

In one embodiment of the present disclosure, the FSH is human FSH.

In one embodiment of the present disclosure, the amino acid sequence of the FSH α-subunit is as set forth in SEQ ID NO: 1.

In one embodiment of the present disclosure, the amino acid sequence of the FSH β-subunit is as shown in SEQ ID NO: 4.

In one embodiment of the present disclosure, the amino acid sequence of the Fc fragment of an antibody is as shown in SEQ ID NO: 7.

In one embodiment of the present disclosure, the β-subunit is linked to the Fc fragment directly.

In one embodiment of the present disclosure, the β-subunit is linked to the Fc fragment directly or via at least one linker (also referred to as a linking element). The linker is optional, which can be inserted between the bioactive molecule and the immunoglobulin constant region. The methods for designing the sequence of the linker are well known in the art. The linker can be attached to the N- or C-terminal of the Fc fragment. The linker can be attached to the N- or C-terminal of the FSH β-subunit.

The second aspect of the present disclosure relates to a heterodimeric protein formed by assembling one fusion protein chain according to any embodiment of the first aspect of the present disclosure with an Fc chain of an antibody, wherein the Fc chain of an antibody is associated with the Fc fragment in the fusion protein by chemical association.

In one embodiment of the present disclosure, the heterodimeric protein comprises three peptide chains of the following formula:

αXXX@βXXX-L-Fc:Fc, wherein, "XXX" refers to FSH, LH, HCG or TSH; "α" refers to α-subunit; "@" represents the correlation between the α-subunit chain and the β-subunit chain, i.e., intermolecular interaction; "β" refers to β-subunit; "L" represents the linking between the β-subunit and the Fc, i.e., direct linking or indirect linking via a linker; "Fc" refers to the Fc fragment of an immunoglobulin; and the colon (:) refers to the chemical association between the βXXX-L-Fc chain and the Fc chain in the fusion protein.

In one embodiment of the present disclosure, the heterodimeric protein has the following formula:

Ta-αXXX@βXXX-L-Fc:Fc or Ta-Fc:Fc-L-βXXX@αXXX, preferably Ta-αXXX@βXXX-L-Fc:Fc, wherein, "XXX" refers to FSH, LH, HCG or TSH; "α" refers to α-subunit; "@" represents the correlation between the α-subunit chain and the β-subunit chain, i.e., intermolecular interaction; "β" refers to β-subunit; "L" represents the linking between the β-subunit and the Fc, i.e., direct linking or indirect linking via a linker; "Fc" refers to the Fc fragment of an immunoglobulin; the colon (:) refers to the chemical association between the βXXX-L-Fc chain and the Fc chain in the fusion protein; and "Ta" refers to an additional active protein or a tag to facilitate the purification of the heterodimeric protein, e.g., a FLAG tag, a histidine tag, a GST tag, or a maltose-binding protein tag.

In one embodiment of the present disclosure, the heterodimeric protein is an FSH heterodimeric protein of the following formula:

αFSH@βFSH-L-Fc:Fc wherein, "αFSH" refers to the α-subunit of FSH; "@" represents the correlation between the α-subunit chain and β-subunit chain of FSH, i.e., intermolecular interaction; "βFSH" refers to the β-subunit of FSH; "L" represents the linking between the FSH β-subunit and the Fc, i.e., direct linking or indirect linking via a linker; "Fc" refers to the Fc fragment of an immunoglobulin; and the colon (:) refers to the chemical association between the βFSH-L-Fc chain and the Fc chain in the fusion protein.

In one embodiment of the present disclosure, the FSH heterodimeric protein is as shown in FIG 1a.

The third aspect of the present disclosure relates to a homodimeric protein formed by complexing two fusion proteins according to any embodiment of the first aspect of the present disclosure, wherein the Fc fragments of the two fusion proteins are linked to each other by chemical association.

In one embodiment of the present disclosure, the homodimeric protein has the following formula:

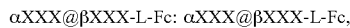
αXXX@βXXX-L-Fc: αXXX@βXXX-L-Fc, wherein, "XXX" refers to FSH, LH, HCG or TSH; "α" refers to α-subunit; "@" represents the correlation between the α-subunit chain and the β-subunit chain, i.e., intermolecular interaction; "β" refers to β-subunit; "L" represents the linking between the β-subunit and the Fc, i.e., direct linking or indirect linking via a linker; "Fc" refers to the Fc fragment of an immunoglobulin; and the colon (:) refers to the chemical association between the two αXXX@βXXX-L-Fc fusion proteins.

In one embodiment of the present disclosure, the homodimeric protein has the following formula:

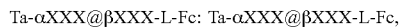
Ta-αXXX@βXXX-L-Fc: Ta-αXXX@βXXX-L-Fc, wherein, "XXX" refers to FSH, LH, HCG or TSH; "α" refers to α-subunit; "@" represents the correlation between the α-subunit chain and the β-subunit chain, i.e., intermolecular interaction; "β" refers to β-subunit; "L" represents the linking between the β-subunit and the Fc, i.e., direct linking or indirect linking via a linker; "Fc" refers to the Fc fragment of an immunoglobulin; the colon (:) refers to the chemical association between the two αXXX@βXXX-L-Fc fusion proteins; and "Ta" is an additional active protein or a tag to facilitate the purification of the homodimeric protein, e.g., a FLAG tag, a histidine tag, a GST tag, or a maltose-binding protein tag.

In one embodiment of the present disclosure, the homodimeric protein is an FSH homodimeric protein of the following formula:

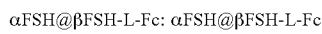
αFSH@βFSH-L-Fc: αFSH@βFSH-L-Fc wherein,"αFSH" refers to the α-subunit of FSH; "@" represents the correlation between the α-subunit chain and β-subunit chain of FSH, i.e., intermolecular interaction; "βFSH" refers to the β-subunit of FSH; "L" represents the linking between the FSH β-subunit and the Fc, i.e., direct linking or indirect linking via a linker; "Fc" refers to the Fc fragment of an immunoglobulin; and the colon (:) refers to the chemical association between the two αFSH@βFSH-L-Fc fusion proteins.

In one embodiment of the present disclosure, the FSH homodimeric protein is as shown in FIG. 1b.

The fourth aspect of the present disclosure relates to a mixture comprising the heterodimeric protein according to any embodiment of the second aspect of the present disclosure and the homodimeric protein according to any embodiment of the third aspect of the present disclosure.

The fifth aspect of the present disclosure relates to a composition comprising the fusion protein according to any embodiment of the first aspect of the present disclosure, the protein according to any embodiment of the second or third aspect of the present disclosure, or the mixture according to the fourth aspect of the present disclosure, and optionally a pharmaceutically acceptable carrier or excipient.

In one embodiment of the present disclosure, the composition is a pharmaceutical composition.

The sixth aspect of the present disclosure relates to a recombinant expression vector comprising a nucleotide sequence encoding the α-subunit of a trophic hormone protein, a nucleotide sequence encoding a fusion protein formed by the β-subunit of the trophic hormone protein and an Fc fragment of an antibody, and a nucleotide sequence encoding an Fc fragment of an antibody, wherein each of the protein chains is transcribed independently, and the trophic hormone is selected from the group consisting of luteotropic hormone, follicle stimulating hormone, chorionic gonadotropin and thyroid stimulating hormone.

In one embodiment of the present disclosure, the trophic hormone is FSH.

In one embodiment of the present disclosure, the nucleotide sequence encoding the α-subunit of the trophic hormone protein is as set forth in SEQ ID NO: 2.

In one embodiment of the present disclosure, the nucleotide sequence encoding the fusion protein formed by the β-subunit of the trophic hormone protein and the Fc fragment of an antibody is as set forth in SEQ ID NO: 4.

In one embodiment of the present disclosure, the nucleotide sequence encoding the Fc fragment of an antibody is as set forth in SEQ ID NO: 6.

The seventh aspect of the present disclosure relates to a recombinant cell comprising the recombinant expression vector according to any embodiment of the sixth aspect of the present disclosure.

In the present disclosure, the cell is a eukaryotic expression cell, e.g., a yeast cell, or a mammalian cell. In one embodiment of the present disclosure, the cell is a mammalian cell (e.g., a HEK293 cell, a CHO cell).

The present disclosure also relates to a method for preparing the mixture according to any embodiment of the fourth aspect of the present disclosure, which comprises the step of expressing a protein with the recombinant expression vector according to any embodiment of the sixth aspect of the present disclosure or with the recombinant cell according to any embodiment of the seventh aspect of the present disclosure.

The present disclosure also relates to a method for preparing a heterodimer according to any embodiment of the second aspect of the present disclosure, which comprises the step of isolating and purifying the mixture according to any embodiment of the fourth aspect of the present disclosure to obtain the heterodimer according to any embodiment of the second aspect of the present disclosure.

In one embodiment of the present disclosure, the method for separation and purification comprises FcRn affinity purification followed by high-resolution strong anion chromatography so as to obtain the heterodimeric protein with a relatively high purity.

The present disclosure also relates to use of the fusion protein according to any embodiment of the first aspect, the protein according to any embodiment of the second or third aspect, the mixture according to any embodiment of the fourth aspect, or the composition according to any embodiment of the fifth aspect of the present disclosure for preparing a trophic hormone pharmaceutical formulation with a prolonged half-life, wherein the trophic hormone is selected from the group consisting of luteotropic hormone, follicle stimulating hormone, chorionic gonadotropin and thyroid stimulating hormone.

In one embodiment of the present disclosure, the trophic hormone is FSH.

The present disclosure also relates to use of the fusion protein according to any embodiment of the first aspect, the protein according to any embodiment of the second or third aspect, the mixture according to any embodiment of the fourth aspect, or the composition according to any embodiment of the fifth aspect of the present disclosure in the manufacture of a medicament for preventing or treating various indications associated with trophic hormones.

The present disclosure also relates to a method for preventing or treating various indications associated with trophic hormones, which comprises the step of administering to a mammal in need thereof an effective amount of the fusion protein according to any embodiment of the first aspect, the protein according to any embodiment of the second or third aspect, the mixture according to any embodiment of the fourth aspect, or the composition according to any embodiment of the fifth aspect.

In the present disclosure, the various indications associated with trophic hormones are well known in the art. FSH can be used to provide beneficial effects (e.g., enhanced fertility) to subjects suffering from such abnormalities, to cure FSH abnormality or dysgenesis. It can be used, for example, in combination with ovulation induction or an assisted reproductive technique (ART), to stimulate folliculogenesis. It can also be used to induce generation of a single follicle during ovulation induction (OI) or generation of a small number of follicles during intrauterine insemination (IUI), for internal insemination. Further, it can also be used for controlled ovarian hyperstimulation (COH).

HCG can be used for infertilitasfeminis, corpus luteum insufficiency, functional uterine bleeding, cryptorchidism, male hypogonadism, threatened abortion, habitual abortion and the like.

LH can be used to promote ovulation and development of the corpus luteum. Formales, it can be used to stimulate Leydig cells to secrete testosterone, can be used to test the functions of Leydig cells, and to promote spermatogenesis when administered in a long term.

TSH can be used to inhibit and ablate postoperative residual cancer tissue in patients with thyroid cancer.

In the present disclosure, a mammal is, for example, a human, a monkey, a mouse, a rat, a sheep, a swine, a horse or the like.

In the present disclosure, the Fc fragment of an antibody refers to the constant region of a human immunoglobulin chain, particularly the carboxyl end of the constant region of an immunoglobulin heavy chain or a portion thereof. For example, the Fc region of an immunoglobulin may comprise two or more domains of heavy chain CH1, CH2, CH3 and CH4, and optionally an immunoglobulin hinge region. According to the amino acid sequence of the heavy chain constant region, immunoglobulins can be divided into different categories and there are mainly 5 classes of immunoglobulins: IgA, IgD, IgE, IgG and IgM, some of which can be further divided into several subclasses (isotypes), e.g., IgG-1, IgG-2, IgG-3, IgG-4, IgA-1 and IgA-2. Selecting a particular immunoglobulin Fc region from a specific class or subclass of immunoglobulins is well within the knowledge of those skilled in the art.

In a specific embodiment of the present disclosure, the Fc fragment of an antibody refers to the Fc fragment of a human immunoglobulin, which comprises at least one hinge region, one CH2 domain and one CH3 domain of the immunoglobulin. Specifically, it can be IgG1 Fc.

In the present disclosure, the intermolecular interactions between the α-subunit chain and the β-subunit chain refer to, for example, ionic interaction, hydrophobic interaction, hydrophilic interaction, van der Waals interaction and hydrogen bonding.

In the present disclosure, the chemical association, i.e., (:), is a covalent bond or non-covalent bond, e.g., at least one non-peptide bond. In certain embodiments, the chemical association is a covalent bond, e.g., a disulfide bond. In other embodiments, the chemical association is a non-covalent bond, e.g., ionic interaction, hydrophobic interaction, hydrophilic interaction, van der Waals interaction and hydrogen bonding. In a particular embodiment of the present disclosure, the chemical association refers to interaction between the two Fc chains.

In the present disclosure, the β-subunit is linked to the Fc fragment via a linker (also referred to as a linking element). The linker is optional, which can be inserted between the bioactive molecule and the immunoglobulin constant region. The methods for designing the sequence of the linker are well known in the art. The linker can be attached to the N- or C-terminal of the Fc fragment. The linker can be attached to the N- or C-terminal of the FSH β-subunit.

In female mammals, the major physiological effect of FSH is to stimulate the development of follicles and ovulation. The FSH as described in the present disclosure is preferably human FSH. According to the sequence homology between human FSH and FSHs from other animals such as murine, swine, sheep etc. (see FIG. 2), FSH also has a very high homology in other animals. Therefore, the FSH as described herein may also be an FSH from other animals, such as murine, swine, sheep, etc. The conservation of LH, HCG and TSH hormones are similar to that of FSH.

In the present disclosure, various alterations can be made to the amino acid sequence of each protein in the complex protein or the DNA coding sequence thereof, without significantly diminishing the activity, function or effect of the complex protein of the present disclosure. The derivatives, analogs or mutants resulting from such alterations as well as uses of such derivatives are all within the scope of the present invention.

The trophic hormone fusion protein involved in the present disclosure can be purified from host cells with routine experimentations. For example, since the FSH-Fc fusion protein comprises an Fc, the protein can be purified using Protein A. The purification methods include, but not limited to, chromatography technologies, such as size exclusion, ion exchange, affinity chromatograph, and ultrafiltration. Methods for isolating and purifying the fusion protein involved in the present disclosure also include appropriate combinations of the various methods as described above.

The trophic hormone fusion protein comprises Fc, preferably human immunoglobulin Fc. In general, the CH3 region polypeptide of human immunoglobulin Fc region is derived from a wild-type human immunoglobulin Fc region. The wild-type human immunoglobulin Fc refers to an amino acid sequence present in human population, and there would naturally be some slight differences in the Fc sequences among individuals. The human immunoglobulin Fc of the present disclosure also comprises certain amino acid modifications of the wild-type human immunoglobulin Fc sequence, e.g., alterations of certain amino acids in the Fc region, including, for example, mutations of amino acid at one or more glycosylation site, or other silent mutations, and amino acid alterations resulting from mutation according to a "knob-hole" model.

Mammalian host cells involved in the present disclosure include, but not limited to, CHO, 293, and myeloma cells. Host cells can also be yeasts or prokaryotic cells, such as *E. Coli*.

In specific embodiments of the present disclosure, an FSH-Fc fusion protein was constructed, wherein the FSH can be substituted with LH, TSH, HCG or other trophic hormones. FSH, together with luteotropic hormone (LH), thyroid stimulating hormone (TSH), and human chorionic gonadotropin (HCG) secreted from placenta, constitutes a glycoprotein family. They all consist of α-subunit and β-subunit, while the α-subunits are identical among these hormones, the β-subunits have characteristics specific to each respective hormone. These β-subunits have very high homology to the FSH β-subunit (FIG. 3), and the contact interfaces between the α-subunits and β-subunits of the ligands and their receptors are similar (the grey areas in FIG. 3), all located at the C-terminals of the α-subunit and β-subunit.

According to the design of the present disclosure, isolating the α-subunit and linking it to the β-subunit via intermolecular interactions have overcome the problem of loss of affinity after linking an α-subunit to a β-subunit via a linker.

In a related aspect of the present disclosure, the pharmaceutical composition comprising the trophic hormone fusion protein such as the FSH-Fc fusion protein herein is used as a drug for treating a disease, a disorder or a condition. In another aspect, the polypeptide or pharmaceutical composition of the present disclosure is used in a method for treating a mammal, particularly human, which comprises administering the polypeptide or pharmaceutical composition to the mammal in need thereof.

It will be appreciated by those skilled in the art that the effective amount of the polypeptide, pharmaceutical formulation or composition of the present disclosure depends on the type of the disease, dosage, dosing scheme, whether the polypeptide, formulation or composition is administered alone or in combination with other therapeutic agents, the serum half-life of the composition, and the general conditions of the patient. In general, the effective amount of the formulation or composition of the present disclosure can ensure achieving a therapeutic effect.

The trophic hormone fusion protein according to the present disclosure can be formulated into a pharmaceutical composition, which can comprise a pharmaceutically acceptable excipient, carrier, buffering agent, stabilizer or other materials well known to those skilled in the art. Such materials should be non-toxic and should not interfere with the efficacy of active ingredients. Such materials may include, for example, any or all of solvents, dispersion media, coatings, antibacterial and antifungal agents, isotonic agents, absorption delaying agents, physiologically compatible substances, and so on. A pharmaceutically acceptable carrier can be, for example, water, saline, phosphate buffered saline, glucose, glycerol, ethanol or the like, or a combination thereof. In some cases, the pharmaceutical composition may comprise an isotonic agent, for example, a sugar, a polyol such as mannitol and sorbitol, or preferably sodium chloride. The pharmaceutically acceptable substances may also be humectant or a small amount of auxiliary substances, such as humectant or emulsifying agents, preservatives or buffering agents, which increase the shelf life or efficacy of the antibody. The exact properties of the carriers or other materials will depend on the administration route, which may be oral, topical, by inhalation or injection, such as intravenous. In a preferred embodiment, the pharmaceutical composition is administered by intravenous infusion or injection. In another preferred embodiment, the pharmaceutical composition is administered by intramuscular or subcutaneous injection.

A pharmaceutical composition for oral administration can be in the form of a tablet, capsule, powder or liquid, which, for example, may comprise an inert excipient or an assimilable edible carrier. A tablet may comprise a solid carrier such as gelatin or an adjuvant. A liquid pharmaceutical composition typically comprises a liquid carrier such as water, petroleum, animal or vegetable oil, mineral oil or synthetic oil; and may comprise a physiological saline solution, a solution of glucose or other saccharides, or a glycol such as ethylene glycol, propylene glycol or polyethylene glycol. A specific binding member (when present, as well as other ingredients) may also be encapsulated in a hard- or soft-shell gelatin capsule, compressed into a tablet, or directly incorporated into a subject's diet. For oral administration, the active ingredient can be blended with an excipient, and then used in the form of an absorbable tablet, buccal tablet, lozenge, capsule, elixir, suspension, syrup, cachet or the like. In order to administer the compound of the present disclosure through routes other than parenteral administration, it may be necessary to coat the compound with a material preventing its inactivation or to co-administer the compound and the material.

For intravenous injection or injection at a sensible site, the active ingredient will be in the form of a parenterally acceptable aqueous solution, which may be pyrogen-free and may have a suitable pK, isotonicity and stability. Those skilled in the art will be able to easily prepare a suitable solution, for example, by using an isotonic vehicle such as a sodium chloride injection, Ringer's injection, or lactate Ringer's solution. If desired, a preservative, stabilizer, buffering agent, antioxidant and/or other additives can be included.

A pharmaceutical composition of the present disclosure can be formulated in the form of a liquid, semi-solid or solid, such as a liquid solution (e.g., an injectable and infusion solution), dispersion or suspension, tablet, pill, powder, liposome and suppository. The preferred forms depend on the desired administration form, therapeutic application, physical and chemical properties and manner of delivery of the molecule. The formulation may comprise an excipient, or a combination of excipients, for example, a carbohydrate, amino acid, and surfactant. A liquid formulation may comprise a wide range of protein concentration and pH value. A solid formulation can be produced by, for example, lyophilization, spray drying, or drying with supercritical fluid technology.

Pharmaceutical compositions typically shall be sterile and stable under conditions for manufacture and storage. A pharmaceutical composition can be formulated as a solution, microemulsion, dispersion, liposome, or other ordered structures suitable for high drug concentration. Sterile injectable solutions can be prepared by mixing an antibody or an antigen binding fragment thereof, a composition or an isolated nucleic acid molecule of the present disclosure in the required amount in an appropriate solvent with one ingredient or a combination of ingredients as enumerated above, as appropriate, followed by filtered sterilization. Generally, dispersions are prepared by incorporating the active compound into a sterile vehicle which may contain a basic dispersion medium and other ingredients from those enumerated above as appropriate. For a sterile powder used to prepare a sterile injectable solution, preferred preparation methods include vacuum drying and lyophilization, which can produce a powder comprising an active ingredient and any additional ingredient needed from a previously sterile-filtered solution. A proper fluidity can be maintained, for example, by the use of a coating, such as lecithin, by maintaining a required particle size in the case of a dispersion, and by the use of surfactants. Prolonged absorption of the injectable compositions can be achieved by including in the compositions an agent that delays absorption, e.g., monostearate salts and gelatin.

In certain embodiments, the pharmaceutical composition as described in the present disclosure can be prepared with carriers that will protect the active ingredient from being rapidly released, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, for example, Sustained and Controlled Release Drug Delivery Systems (J. R. Robinson, ed., Marcel Dekker, Inc., New York, 1978).

The pharmaceutical composition of the present disclosure can be administered alone or in combination with other therapies, simultaneously or sequentially, depending on the condition to be treated.

The pharmaceutical composition can be used in combination with other therapeutic agents. These agents can be mixed into the pharmaceutical composition as a part thereof, can be administered with the polypeptide separately and simultaneously, or can be used according to other acceptable treatment regimens. In addition, the polypeptide, formulation or pharmaceutical composition can be used as an adjuvant to other medicaments.

The range of treatment involved in the present disclosure is associated with the therapeutic effects of the trophic hormones. The fusion protein, heterodimeric protein or pharmaceutical composition comprising the above proteins of the present disclosure can be used to treat any corresponding indications relating to trophic hormones, including, for example, to reduce the severity of any reproductive disorders or disease conditions responsive to a treatment with the pharmaceutical composition; to prevent one or more symptoms associated with these disorders or disease conditions; to reduce the course of treatment of an FSH abnormality; to provide subjects suffering from these abnormalities with beneficial effects (e.g., enhanced fertility); to cure FSH abnormalities or reproductive disorders; to stimulate folliculogenesis, for example, when used in combination with ovulation induction or assisted reproductive technique (ART); to induce the generation of a single follicle during ovulation induction (OI) or a small number of follicles during intrauterine insemination (IUI) for internal insemination; or to be used for controlled ovarian hyperstimulation (COH). The present disclosure provides a method for fusing an FSH-Fc fragment to increase the in vivo half-life of the FSH without loss of its in vivo activity. Specifically, a β-subunit of the FSH is fused to a Fc fragment, and the α-subunit of the FSH is transcribed and translated separately, making use of the association between the FSH α- and β-subunits. The present disclosure will provide part of or all of the effects associated with the treatment with FSH, can be administered less frequently than existing FSH products, and can provide a more stable FSH activity as compared to that achievable by existing therapies.

The range of the treatment involved in the present disclosure also includes treatment of infertilitas feminis, corpus luteum insufficiency, functional uterine bleeding, cryptorchidism, male hypogonadism, threatened abortion, habitual abortion and the like, for example, for promoting ovulation and development of the corpus luteum, and for stimulating Leydig cells of males to secrete testosterone, for testing the functions of Leydig cells, and for promoting spermatogenesis when administered in long-term. The range of the treatment involved in the present disclosure also includes inhibition and ablation of postoperative residual cancer tissue in patients with thyroid cancer.

Beneficial Effects

Comparing to patent US20050186662, in the present disclosure, α-subunit of gonadotropin or thyroid stimulating hormone is isolated, and binds to a β-subunit via the intermolecular interactions between them, so that the gonadotropin or thyroid stimulating hormone can bind to their corresponding receptors normally, thereby retaining the in vivo activity thereof to the largest extent while increasing their in vivo half-life.

BRIEF DESCRIPTION OF THE DRAWINGS

Figure 2:
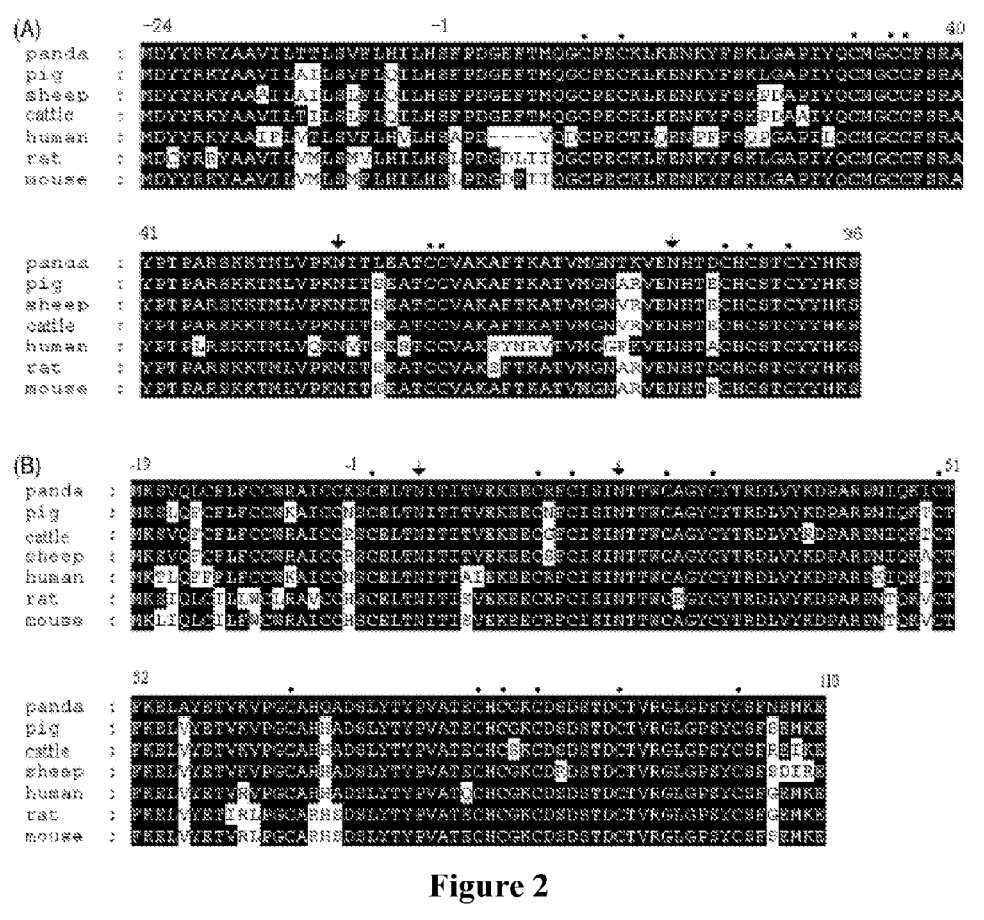

FIG. 2 shows multiple sequence alignment of FSHα (panel A) and FSHβ(panel B) derived from different species. The sequences are obtained from NCBI GenBank. Human (V00518, NM000510, NM000894), cattle (X00050, M14853, M10077), sheep (X16977, X15493, X52488), pig (D00768, AF134151, D00579), rat (V01252, M36804, D00576), and mouse (J00643, NM00804, AF33067). Figure discloses Panel A as SEQ ID NOS 13-19 and Panel B as SEQ ID NOS 20-26, respectively, in order of appearance.

DETAILED DESCRIPTION OF THE INVENTION

Figure 1:
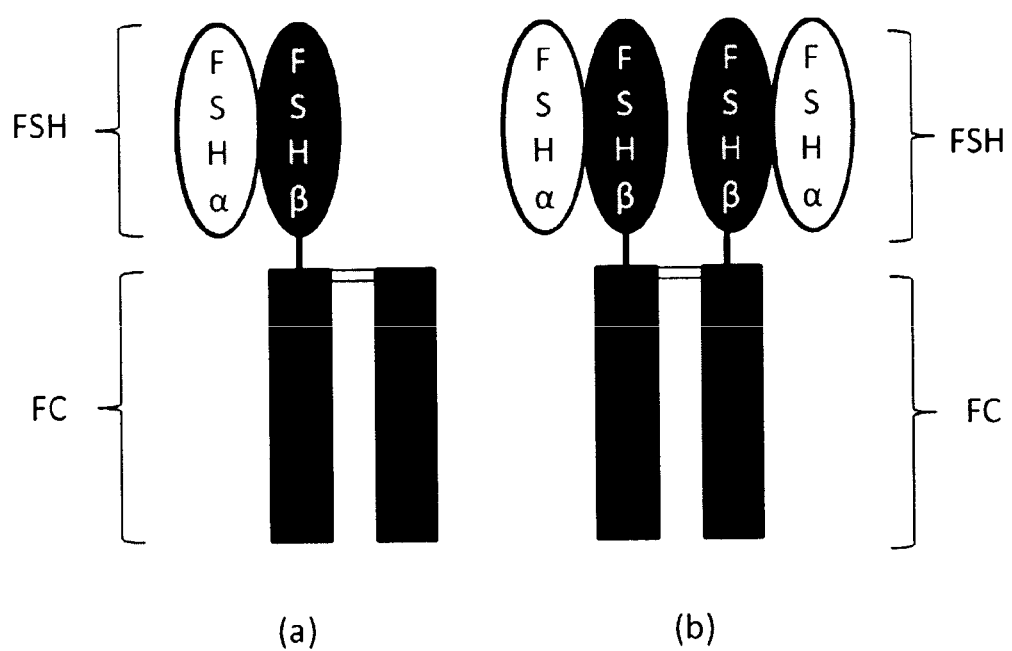
FIG. 1 is a schematic diagram illustrating a FSH-Fc fusion protein heterodimer and a FSH-Fc fusion protein homodimer.
Figure 3:
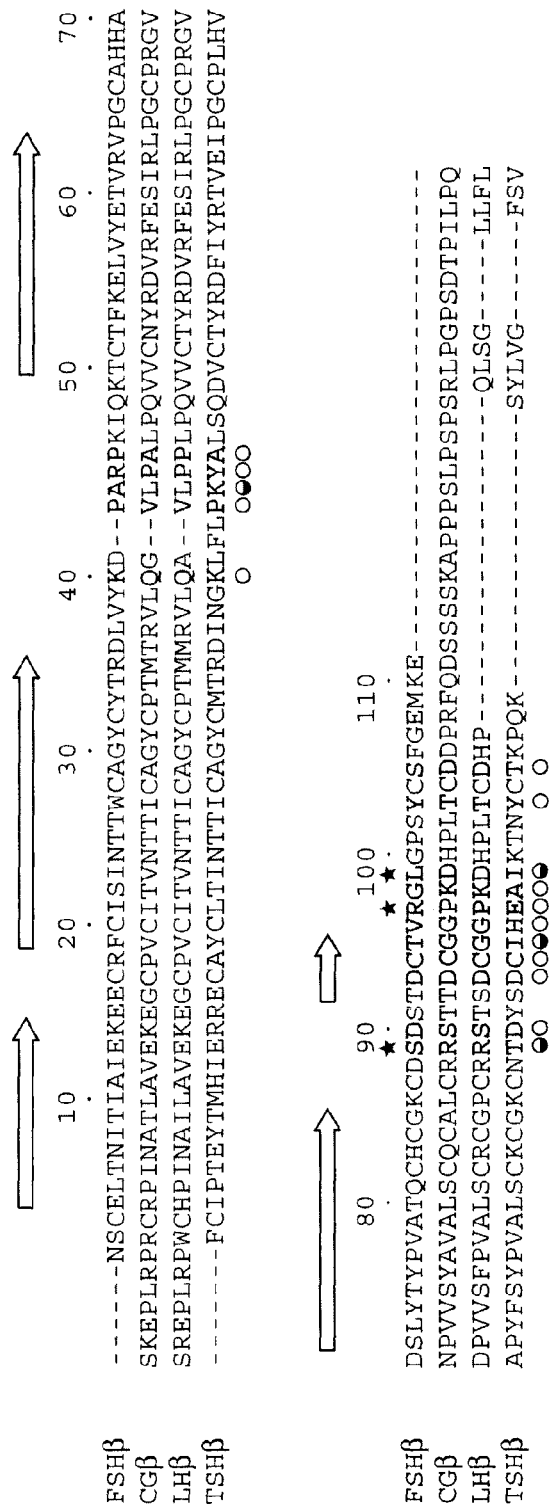
FIG. 3 shows multiple sequence alignment among human FSH, CG, LH and TSH β chains, wherein the buried amino acids and the receptor-ligand binding regions of FSHβ are highlighted in grey. Figure discloses SEQ ID NOS 27-30, respectively, in order of appearance.

The embodiments of the present disclosure will be described in detail with reference to the examples hereinafter. However, those skilled in the art will appreciate that the following examples are intended to illustrate the present invention only, and shall not be construed as limiting the scope of the present invention. Those examples in which specific conditions were not specified were conducted according to conventional conditions or the conditions recommended by the manufacturer. All the reagents or instruments without specified manufacturers are conventional and commercially available products.

EXAMPLE 1.

Construction of Plasmids for FSH-Fc Homodimer and FSH-Fc/Fc Heterodimer

1. Construction of the Plasmid for FSH-Fc Homodimer

Modifying the commercial mammalian cell expression vector pcDNA4/myc-HisA. The commercial vector pcDNA4/myc-HisA (Invitrogen, V863-20) comprises two Pvu II restriction sites, located at about 1,411 bp and 3,160 bp, respectively. The plasmid was subjected to site-directed mutagenesis, so that the base located at 3,106 bp was mutated from C to G to remove the Pvu II restriction site at this position, retaining only one restriction site at about 1,411bp. The new vector was designated as pcDNA4m.

According to the gene sequence of human FSHα-subunit (Genebank No. NP_000726.1) retrieved from the Genebank, the corresponding Hind III and EcoRI restriction sites were added to both ends of the gene so as to synthesize the gene encoding human FSHα-protein. The synthesized FSHα gene was subcloned into the modified vector pcDNA4m by double digestion with Hind III and EcoR I, both of which were purchased from Takara. The plasmid thus constructed was verified by sequencing, and the recombinant plasmid DNA obtained was designated as pcDNA4m-FSHα.

The sequence of human FSHα is set forth in SEQ ID NO:1, the sequence of the signal peptide is set forth in SEQ ID NO:2, and the nucleotide sequence encoding the FSHα sequence is set forth in SEQ ID NO:3.

According to the gene sequence of human FSHβ-subunit (Genebank No. NP_000501.1) retrieved from the Genebank and the gene sequence of human IgG1 Fc fragment (hing-CH2-CH3), the gene encoding human FSHβ-Fc fusion protein was synthesized. The corresponding Hind III and EcoRI restriction sites were added to both ends of the synthesized gene sequence. The synthesized FSHβ-Fc gene was subcloned into the modified vector pcDNA4m by double digestion with Hind III and EcoRI, both of which were purchased from Takara. The plasmid thus constructed was verified by sequencing, and the recombinant plasmid DNA obtained was designated as pcDNA4m-FSHβ-Fc.

The sequence of human FSHβ-Fc fusion protein is set forth in SEQ ID NO:4, the sequence of the signal peptide is set forth in SEQ ID NO:5, and the nucleotide sequence encoding the FSHβ sequence is set forth in SEQ ID NO:6. The amino acid sequence of the human IgG1 Fc fragment is set forth in SEQ ID NO:7, and the encoding nucleotide sequence is set forth in SEQ ID NO:8.

Figure 4:
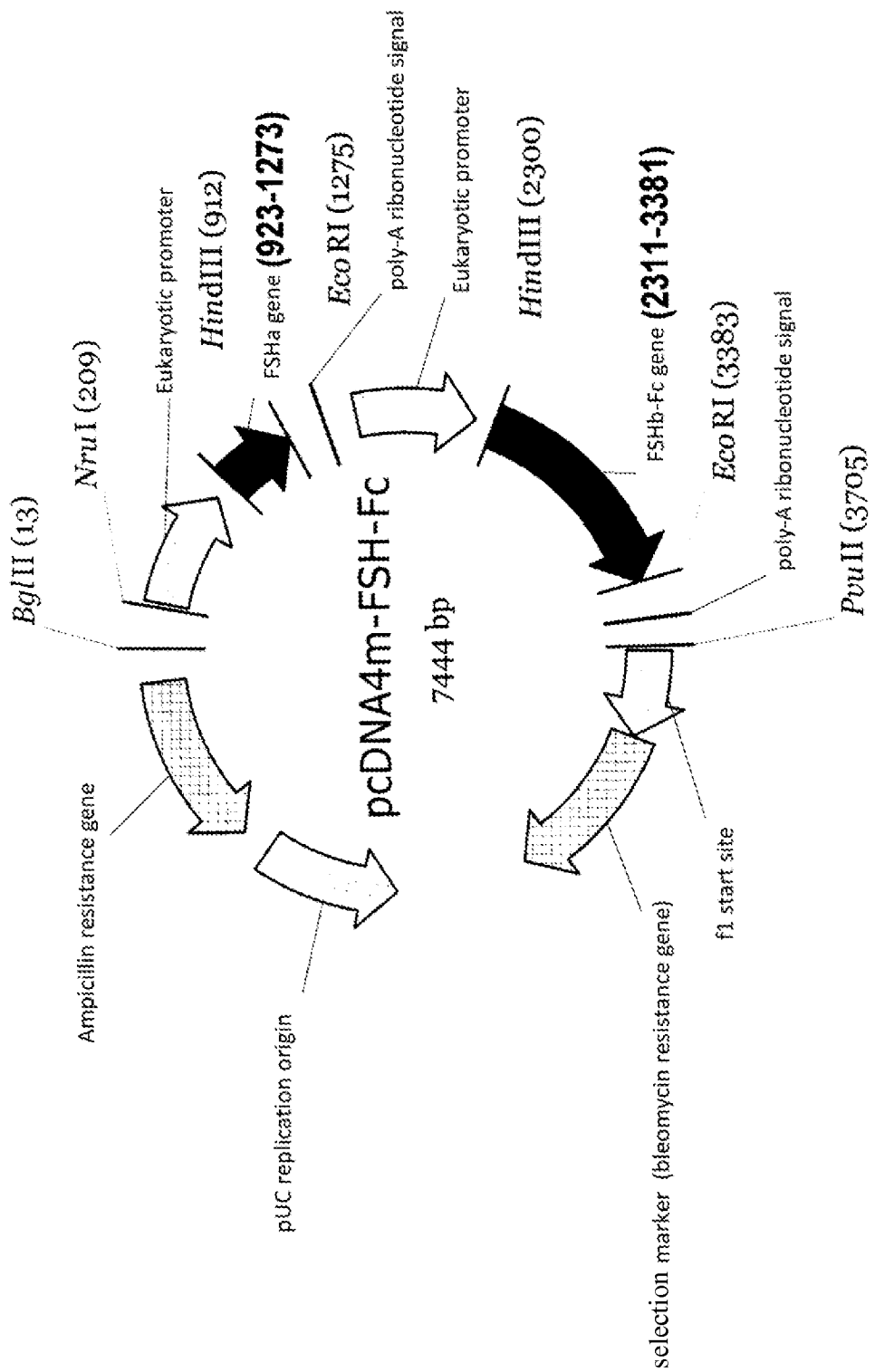
FIG. 4 illustrates a recombinant plasmid for FSH-Fc homodimer.

The single-gene expression vector pcDNA4m-FSHα successfully constructed as above was double digested with Bgl II and Pvu II, both of which were purchased from Takara. The digestion products were separated and purified with 0.8% agarose gel electrophoresis, and the DNA fragment of about 1.6 kb comprising the FSHα gene was recovered. The pcDNA4m-FSHβ-Fc was double digested with Bgl II and Nru I, and the DNA fragment of about 6 kb comprising the FSHβ-Fc gene was recovered. Then, the digested DNA fragments were ligated, and the FSHα and FSHβ-Fc exogenous gene expression elements were integrated into one expression vector to obtain the recombinant plasmid pcDNA4m-FSH-Fc, i.e., the recombinant plasmid for the FSH-Fc homodimer (see FIG. 4).

2. Construction of the Plasmid for FSH-Fc/Fc Heterodimer

Figure 5:
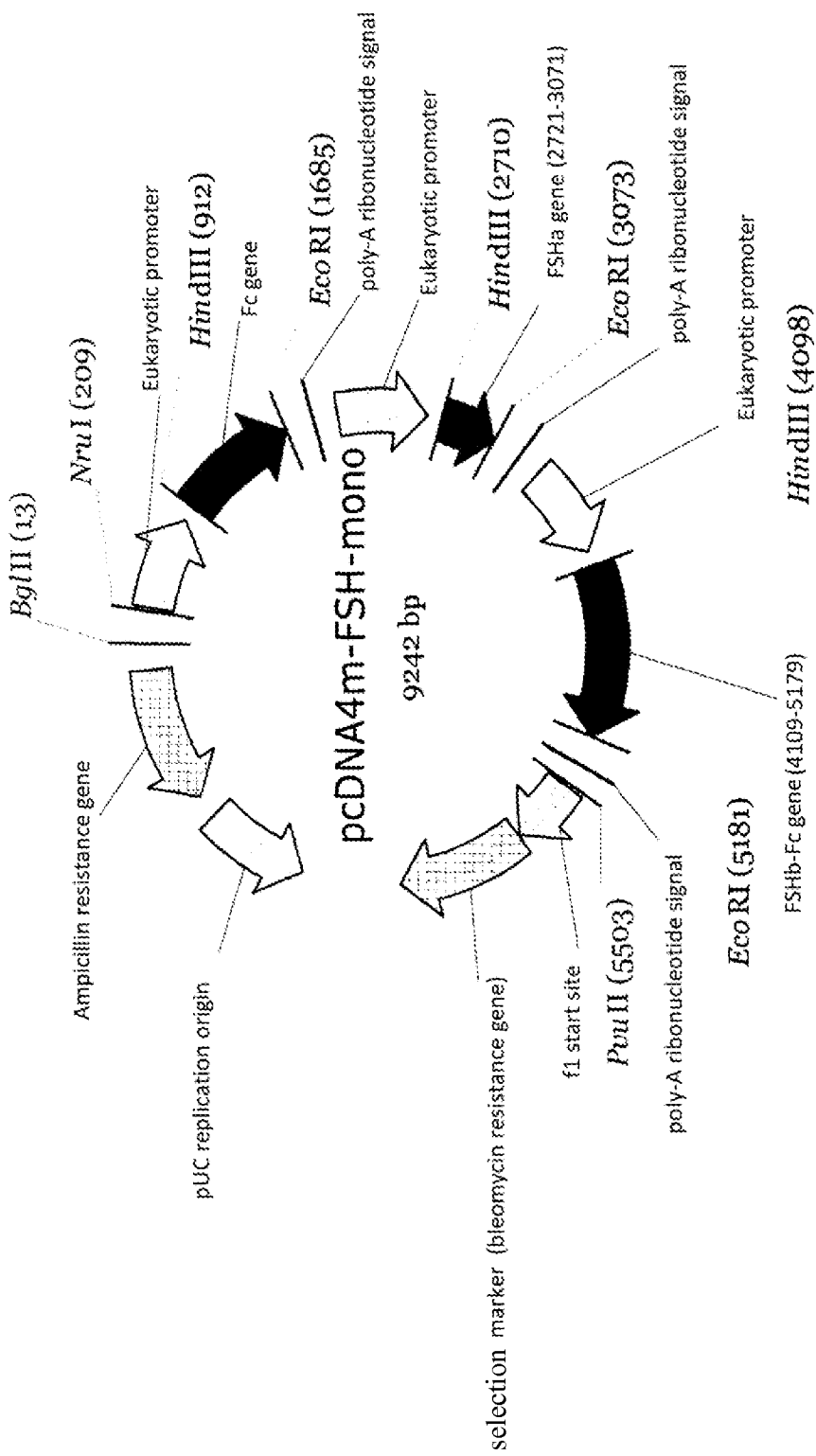
FIG. 5 illustrates a recombinant plasmid for FSH-Fc/Fc heterodimer.

PCR amplification was conducted using designed primers with pcDNA4m-FSHβ-Fc as a template to obtain the Fc gene.AnIgG1 signal peptide (5'METDTLILWRLLLWVPG-STLGSA3' (SEQ ID NO: 12)) was added to the N-terminal of the gene with the use of PCR primers, and Hind III and EcoR I restriction sites were added to both ends of the gene, respectively. The PCR product was subcloned into the modified vector pcDNA4m by double digestion to obtain the recombinant plasmid pcDNA4m-Fc. The recombinant plasmid was double digested with NruI and PvuII, both of which were purchased from Takara. The digestion products were separated and purified with 0.8% agarose gel electrophoresis, and an Fc-containing DNA fragment of about 1.8 kb was recovered. The DNA fragment was ligated into the pcDNA4m-FSH-Fc plasmid that was singly digested with Nru I and dephosphorylated by CIAP via blunt end ligation, so as to obtain the recombinant plasmid pcDNA4m-FSH mono, i.e., the recombinant plasmid for FSH-Fc/Fc heterodimer. The plasmid map is shown in FIG. 5. The FSHα, FSHβ-Fc and Fc genes were constructed into the same plasmid at a molar ratio of 1:1:1, and the finally expressed FSH-Fc and Fc proteins were present in three forms: FSH-Fc homodimer, FSH-Fc/Fc heterodimer and Fc homodimer, with a theoretical molar ratio of 1:2:1.

The recombinant plasmids pcDNA4m-FSH-Fc and pcDNA4m-FSH mono with endotoxin removed were obtained using a Qiagen Midi kit according to the manufacturer's instructions.

EXAMPLE 2.

Expression and Purification of FSH-Fc Homodimeric and FSH-Fc/Fc Heterodimeric Proteins 1. Transient Expression of FSH-Fc Homodimeric and FSH-Fc/Fc Heterodimeric Proteins Two days before transfection, 500 mL of HEK293 (ATCC, CRL-1573™) cells acclimated in suspension were prepared for transient transfection, and seeded at a density of $0.8 \times 10^6$ cells/mL. Two days later, the cells to be transfected in the suspension were counted and the cell density was 3.5-4×10⁶ cells/mL. The cell suspension was centrifuged at 1000 rpm for 5 min, and the supernatant was discarded. The cells were resuspended in 100 mL of fresh Freestyle293 medium, and centrifuged at 1000 rpm for 5 min again. The supernatant was discarded and the 293 cells were resuspended in 500 mL of Freestyle293 medium. 250 µg of pcDNA4m-FSH-Fc and 250 µg of pcDNA4m-FSH mono plasmids were diluted with 2.5 mL of Freestyle293 medium, respectively, and 1.5 mL of PEI (polyethylenimine) was diluted with 5 mL of Freestyle293 medium. 2.5 mL of each plasmid was evenly mixed with 2.5 mL of PEI for 5 minutes at room temperature. The plasmid/PEI mixtures were respectively added to 250 mL of the cell suspension and incubated at 37° C. under 10% $CO_2$ while shaking at 90 rpm; meanwhile, 50 µg/L IGF-1 (insulin growth factor 1) was supplemented. Four hours later, 250 mL of EX293 medium, 2 mM Glutamine and 50 µg/L IGF-1 were supplemented respectively for incubation at 135 rpm. Twenty-four hours later, 3.8 mM VPA (sodium valproate) was added. After incubation for 5-6 days, 500 mL of the supernatants containing the FSH-Fc homodimer and the FSH-Fc/Fc heterodimer were collected for purification.

2. Purification of the FSH-Fc Homodimeric and FSH-Fc/Fc Heterodimeric Proteins

Figure 6:
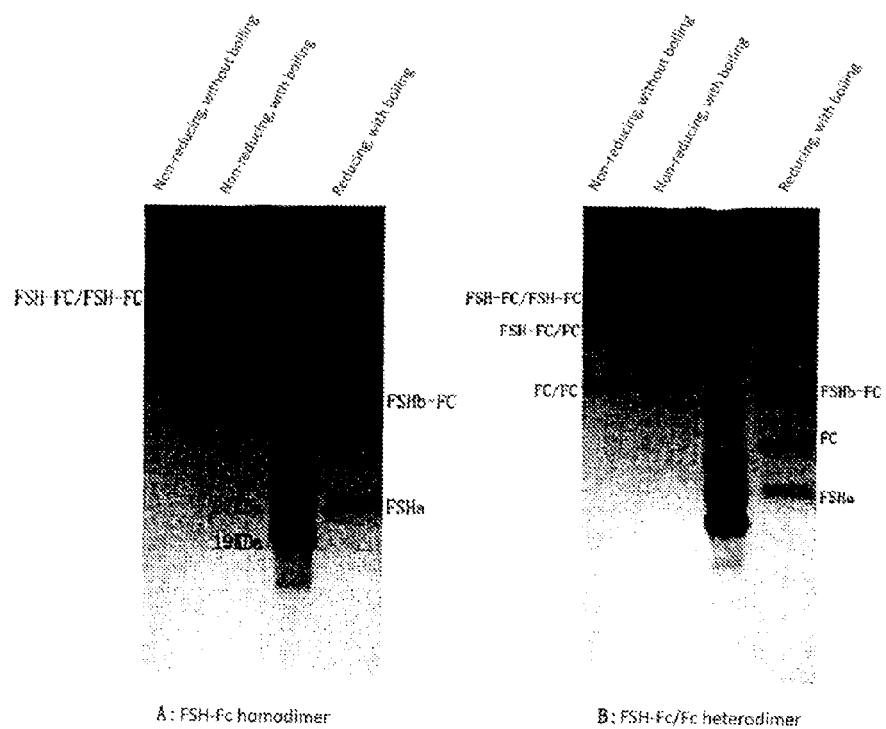
FIG. 6 illustrates SDS-PAGE electrophoretograms of a FSH-Fc homodimer and a FSH-Fc/Fc heterodimer after one-step purification. A: SDS-PAGE electrophoretogram of the FSH-Fc homodimer; B: SDS-PAGE electrophoretogram of the FSH-Fc/Fc heterodimer.

Firstly, murine FcRn (neonatal Fc receptor) protein (Uniprot No.: Q61559) was cross-linked to NHS-activated agarose resin (Thermo). The cell culture was centrifuged, and the supernatant was filtered through a 0.22 µm filter and then loaded onto an FcRn column Then, the column was rinsed with 20 mM PB, 50 mMNaCl, pH 6.2. Finally, the target protein was eluted with 20 mM PB, 50 mMNaCl, pH 7.4. The SDS-PAGE results after one-step purification are shown in FIG. 6. The binding of the Fc fusion protein occurs via disulfide bonds between the Fcs. In the case of non-reducing gel, i.e., without addition of the strong reductant DTT (dithiothreitol), disulfide bonds linking the Fcs are not destroyed so that the fusion protein is present in the form of a dimer. The two subunits of the FSH, i.e., α subunit and β subunit, are bound via a non-covalent bond. In the case where the sample was not boiled and a non-reducing gel was used, the non-covalent bond was not destroyed; while in the case where the sample was boiled and a non-reducing gel was used, the non-covalent bond between the two subunits was broken. Thus, the electrophoresis was conducted with boiled and unboiled samples under reducing and non-reducing conditions, respectively. After one-step purification, the purity of the FSH-Fc homodimeric protein reached above 90%. The proteins expressed from the recombinant plasmid for FSH-Fc/Fc heterodimer were present in the form of a mixture comprising the FSH-Fc homodimer, the FSH-Fc/Fc heterodimer and the Fc homodimer in a molar ratio of approximately 1:2:1, which is consistent with the theoretical expectation (see FIG. 6).

EXAMPLE 3.

Preliminary in vivo Pharmacodynamic Study on a Mixture of FSH-Fc Homodimer and FSH-Fc/Fc Heterodimer in Rats A preliminary in vivo pharmacodynamic study was conducted for the purified FSH-Fc homodimeric protein and FSH-Fc/Fc heterodimeric protein isolated and prepared in Example 2, and rat ovarian weight gain was used as the evaluation model. FSH or molecules having the FSH activity were subcutaneously administered to immature female rats of 21 days old to trigger follicle growth. Such growth can be easily detected by measuring the late stage ovarian weight. This method has been used for decades to calibrate FSH activity for clinical products, it can measure the relevant physiological effects of FSH, and has a clear correlation with the performances of clinical products.

Healthy, qualified female Sprague-Dawley rats of 21 days old were selected and the in vivo animal studies on the FSH-Fc homodimeric protein and FSH-Fc/Fc heterodimeric protein were conducted according to the experimental protocol described in Appendix 121, Volume II of the Chinese Pharmacopoeia (2010 Edition). The dosages of the samples were divided into three groups: high, medium and low (2.5 U, 1.25 U, and 0.5 U, respectively). The control Gonal-F (purchased from Serono) (with an estimated specific activity of 10,000 U/mg) was administered once a day, while the FSH-Fc homodimeric protein and FSH-Fc/Fc heterodimeric protein samples (both with an estimated specific activity of 1,000 U/mg) were administered only once. 72 hours later, the ovaries were weighed and calculated according to the "NIFDC Pharmacopoeia Bioassay Statistics Program BS2000 Version 3.3". The results showed that Gonal-F had a specific activity of 11,000 IU/mg, the FSH-Fc/Fc heterodimeric protein sample had a specific activity of 1,300 IU/mg, and the FSH-Fc homodimeric protein sample had a specific activity of 1,000 IU/mg. The results indicated that as compared to the administration of Gonal-F once a day for three consecutive days, the FSH-Fc/Fc heterodimeric protein still had certain FSH activity when administered only once. According to the product specification of Gonal-F, the recommended clinical dosage is 75 IU, from which it can be inferred that the clinical dosage of the FSH-Fc/Fc heterodimeric protein is about 17 micrograms, which is within the expected dosage range.

EXAMPLE 4.

Preliminary in vivo Pharmacokinetic Study on the FSH-Fc/Fc Heterodimer in Rats

Figure 7:
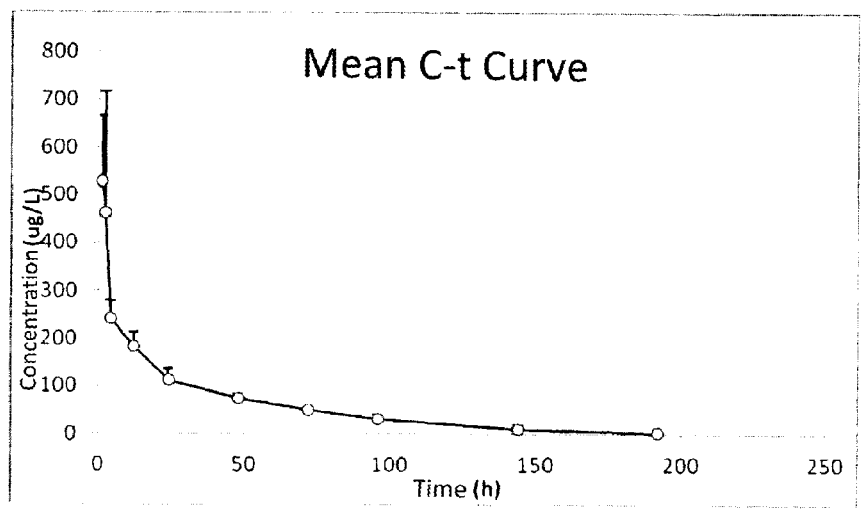
FIG. 7 is a graph showing the concentration-time curve of serum FSH-Fc/Fc from SD rats receiving a single subcutaneous dose of 30 μg/kg of a FSH-Fc/Fc heterodimer.

An in vivo pharmacokinetic study was conducted for active FSH-Fc/Fc heterodimeric protein (see Example 2 for details of sample preparation) in rats. The specific protocol is as follows: female Sprague-Dawley rats of about 6 weeks old received intravenous injection of the FSH-Fc/Fc heterodimeric protein (see Example 2 for details of sample preparation) at a dosage of 30 µg/kg. Blood was collected postorbitally at 0, 1, 2, 4, 12, 24, 48, 72, 96, 144, and 192 hours after administration, with a collection volume of 100 µL each time, and the serum obtained after centrifugation was frozen at −80° C. for ELISA analysis. A sandwich ELISA assay was conducted with an anti-FSH coating antibody (Fitzgerald Industries, Catalog No. 10-F20A) and a horseradish peroxidase-coupled anti-Fc detection antibody (Lakepharma, CatalogNo. 203150), and the results are shown in FIG. 7. The half-life of FSH-Fc/Fc heterodimeric protein was 30-40 hours, while the in vivo half-life of intravenously administered Gonal-F was about 5 h in rats, which indicates that the FSH-Fc/Fc heterodimer has a longer half-life than Gonal-F; specifically, its half-life is 6-8 times longer than that of Gonal-F.

EXAMPLE 5.

Obtaining a Stable Cell Line Highly Expressing FSH-Fc/Fc Heterodimer

According to the results of previous experiments, the FSH-Fc/Fc heterodimeric protein has decent FSH activity, and it has an in vivo half-life of about 30-40 h in rats, more than 3 times of that of the control Gnoal-F, and therefore has a potential for clinical application. Therefore, attempts were made to obtain a cell line stably expressing the FSH-Fc/Fc heterodimer for subsequent process development and commercialization. The specific protocol for obtaining a stable cell line is as follows: HEK293 (ATCC, CRL-1573™) cells in logarithmic growth phase were seeded into a 24-well plate at a concentration of $1\times10^5$ cells/well, and cultured in a complete medium (DMEM containing 10% fetal bovine serum) for 24 h, such that the cells reached 75-85% confluence the next day. The recombinant plasmid pcDNA4m-FSH mono was transfected using Lipofectamine 2000 transfection reagent (Invitrogen, P/N52887). 5 h after transfection, the medium was exchanged, and 400 µl of the complete medium per well was added. 24 hours later, the cells were passaged at a ratio of 1:5 into a cell culture dish containing 10 mL of fresh complete medium. After 24 hours, the medium was replaced by a selection medium (the complete medium containing 200 µg/mL zeocin), and the selection medium was changed very 3-4 days. 4-6 weeks later, single clones were picked and passaged into a 24-well plate. Monoclonal screening was conducted when the cells reached 80-100% confluence after about 4-5 days. The strategy for monoclonal screening is as follows: an Fc ELISA detection kit was used for the first round of detection, and a total of 309 clones were screened. According to the ELISA results and taking into account colony size, 102 clones having a relatively high level of Fc expression were selected, and passaged into a 6-well plate. An FSH ELISA kit (DRG, E1A-1288) was used to measure the expression level of FSH so as to select positive clones. Clones having a relatively high level of FSH expression were selected for non-reducing SDS-PAGE electrophoresis.

Figure 8:
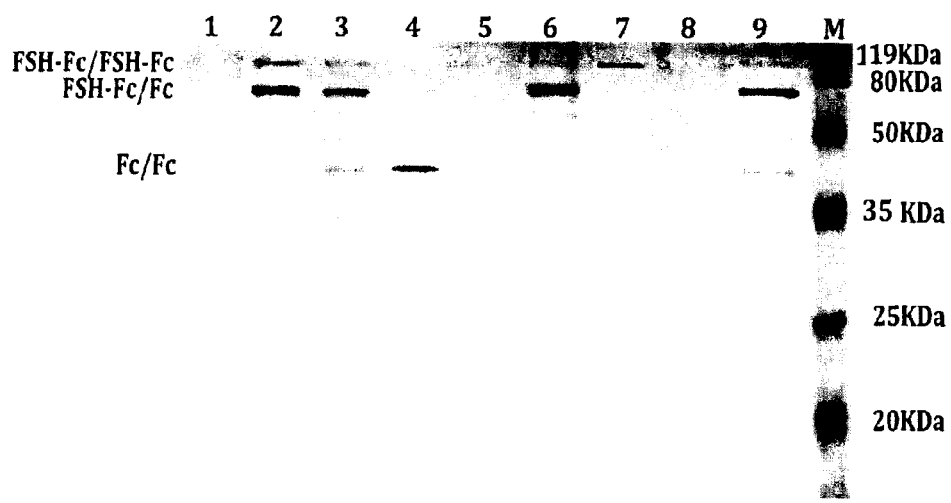
FIG. 8 is a reducing SDS-PAGE electrophoretogram of FSH-Fc/Fc subjected to western blotting.

As mentioned above, the FSHα, FSHβ-Fc and Fc genes were constructed into the plasmid pcDNA4m-FSH-Fc mono at a molar ratio of 1:1:1, and the FSH-Fc and Fc proteins finally expressed were present in three forms: FSH-Fc homodimer, FSH-Fc/Fc heterodimer and Fc homodimer, generally with a molar ratio of 1:2:1. Our final target product is the FSH-Fc/Fc protein, which has FSH activity and an in vivo half-life 3-4 times longer than that of FSH in rats. In addition, with respect to subsequent protein purification process, the separation of the FSH-Fc/Fc heterodimeric protein from the Fc homodimeric protein is much easier than from the FSH-Fc homodimeric protein. Therefore, our screening criteria, assessed by protein electrophoresis were that the FSH-Fc/Fc heterodimeric protein is dominant, while minimum FSH-Fc homodimer present. The non-reducing SDS-PAGE electrophoretogram of part of the clones finally selected is shown in FIG. 8. According to the electrophoretic profile, the clones in Lanes 2, 3, 6 and 9 were selected for subcloing and development of purification process. It is worth mentioning that for the clone in Lane 6, the expression product was present substantially in the form of the FSH-Fc/Fc heterodimer, and the amount of FSH-Fc homodimeric proteins was very little, making the development of subsequent protein purification process fairly simple. The clones in Lanes 2, 3, 6 and 9 were maintained as cell lines: a clone was picked from the 6-well plate, and expanded in a 125 ml shake flask. When the cell density was $2$-$3\times10^6$ cells/ml and the cell viability was greater than 90%, the culture was centrifuged, and complete medium and 7.5% DMSO (dimethyl sulfoxide) were added to the cell pellet, and mixed evenly by gently pipetting to obtain a cell density of $1\times10^7$ cells/ml. The cell suspension was aliquoted into Cryo tubes at 1 ml/tube.

EXAMPLE 6.

Expression and Purification of the FSH-Fc/Fc Heterodimeric Protein

Stable cell lines were expanded in a T75 cell culture flask, and transferred to a shake flask for suspension culturing in CD Opti CHO medium (Invitrogen, Catalog No. 81-011), after the cells grew to about 90% confluence. After 3 weeks of acclimation, the cells grew normally, i.e., the acclimation was completed. The completely acclimated cells were expanded to 1 L, and the supernatant of the culture was harvested. Since FSHα, FSHβ-Fc and Fc were co-expressed, the finally collected solution comprised a mixture of the FSH-Fc homodimer, FSH-Fc/Fc heterodimer and Fc homodimer.

Figure 9:
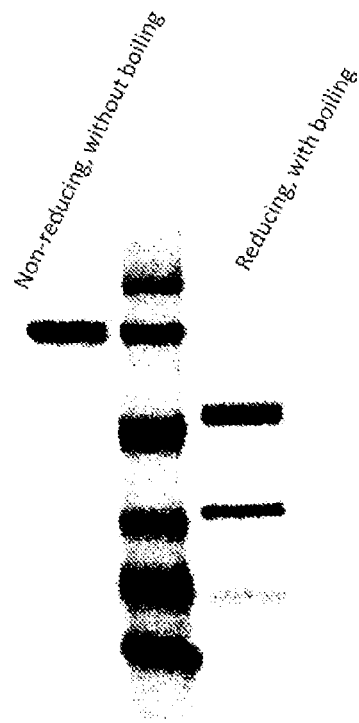
FIG. 9 is an SDS-PAGE electrophoretogram of FSH-Fc/Fc heterodimer finely purified.

Preliminary purification was conducted by FcRn affinity chromatography as described in Example 2. After elution, a small amount of residual FSH-Fc homodimer and all of the Fc homodimer were removed by Source Q (GE healthcare, Catalog No. 17-0947-20). The Source Q chromatographic column was first treated with a regeneration solution (10 mM Tris, 1 mM NaCl, pH 8.0) and an equilibrium solution (10 mM Tris, 50 mM NaCl, pH 8.0). The sample eluted by FcRn was adjusted to pH 8.0 and then loaded directly onto the column The column was re-equilibrated with the equilibrium solution to remove residual Fc homodimer, and the FSH-Fc/Fc heterodimer was eluted with an elution solution (10 mM Tris, 200 mM NaCl, pH 8.0). Finally, the column was rinsed with the regeneration solution to remove residual FSH-Fc homodimer. After FcRn affinity chromatography and Source Q ion exchange chromatography, the FSH-Fc/Fc heterodimer had a very high purity and the SDS-PAGE electrophoretogram is shown in FIG. 9.

EXAMPLE 7.

In Vitro Function of FSH-Fc/Fc Heterodimer

Figure 10:
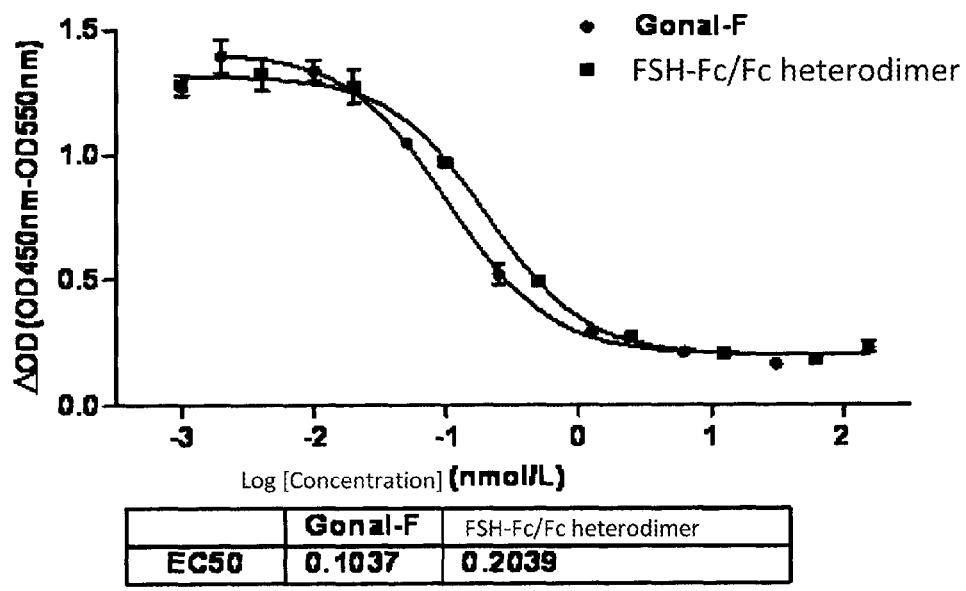
FIG. 10 illustrates comparison of dosage-effect relationship curves between a FSH-Fc/Fc heterodimer and a Gonal-F— the level of cAMP produced via mediation by exogenous FSHR upon in vitro stimulation.

An in vitro biological activity assay was conducted for the purified FSH-Fc/Fc heterodimer isolated and prepared in Example 6, to determine the ability of the FSH-Fc/Fc heterodimer to stimulate CHO cells recombinantly expressing human FSH receptors to produce cyclic adenosine monophosphate (cAMP). CHO-FSH receptor (CHO-FSHR) cells were maintained in FSHR growth medium (minimal medium (DMEM)+10% fetal bovine serum). The CHO-FSHR cells were seeded into a 96-well plate at $2\times10^4$ cells/well, 100 µL/well, incubated at 37° C. for 24 hours before detection, and assayed for activity when the cells reached at least 70% confluence. The sample and the control Gonal F were serially diluted 1:3 from 67.5 nM in the detection medium (minimal medium (DMEM)+10% fetal bovine serum+0.1 mM IBMX (Sigma, 15879-100 mg)). The growth medium was removed from the detection dish, and 25 µL of the detection medium was added. The culture dish was recovered and incubated at 37° C. for 15 minutes. The test sample was added to the wells at 25 µL/well and mixed. After the culture dish was recovered and incubated at 37° C. for 1 hour, the sample and the medium were removed from the wells. Then, 25 µL of standard lysis buffer was added to each well, and the culture dish was covered with a lid and shaken for 5 minutes. After lysis and incubation for 5 minutes, 25 µL of cell lysate was transferred to a cAMP culture dish, and cultured at room temperature for 30 minutes. To each well, 25 µL of cAMP-alkaline phosphatase composition was added, followed by 25 µL of anti-cAMP antibody, and the culture dish was covered with a lid and shaken for 30 minutes at room temperature. The culture dish was then washed 6 times with wash buffer at 350 µL/well. Then, 100µL of substrate enhancer was added to each well, and the culture dish was covered with a lid and incubated in the dark at 25° C. for 30 minutes. Then, each well in the culture dish was read for 1 second, wherein the wells with low cAMP concentration showed high signals, and the wells with high cAMP concentration showed low signals. The dosage-effect relationship curves of the sample FSH-Fc/Fc heterodimer and the control Gonal-F are shown in FIG. 10. The 50% effective concentration ($EC_{50}$) was calculated. The results showed that the $EC_{50}$ of Gonal F was 0.1037 nmol/L and the $EC_{50}$ of FSH-Fc/Fc was 0.2039 nmol/L, indicating that the in vitro biological activity of the FSH-Fc/Fc was about 50% of that of Gonal-F.

EXAMPLE 8.

In vivo Pharmacokinetic Study for FSH-Fc/Fc Heterodimer in Rats

Figure 11:
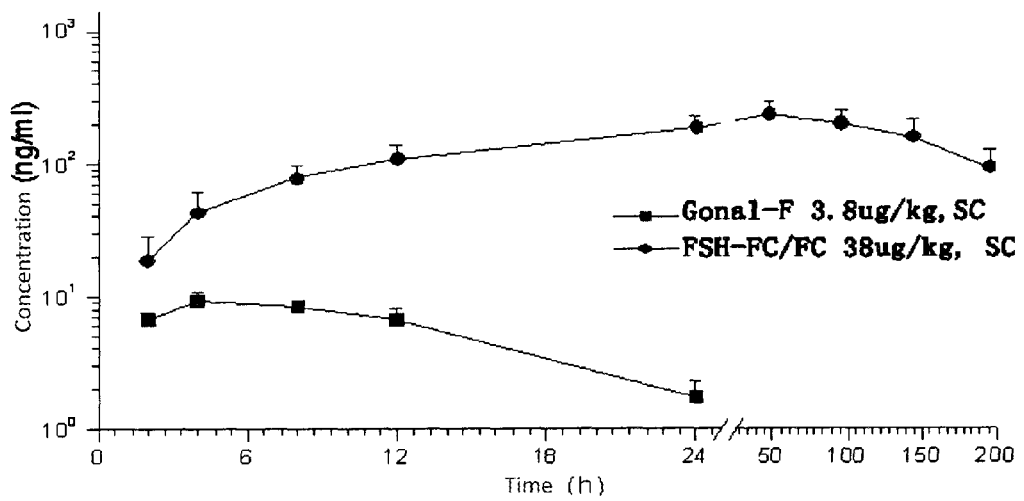
FIG. 11 illustrates comparison between the concentration-time curve of serum FSH-Fc/Fc from SD rats receiving a single subcutaneous dose of 38 μg/kg of FSH-Fc/Fc heterodimer and that of serum FSH from SD rats receiving a single subcutaneous dose of 3.8 μg/kg of the Gonal-F.

An in vivo pharmacokinetic study was conducted for the purified FSH-Fc/Fc heterodimer isolated and prepared in Example 6 in rats. The specific protocol is as follows: female Sprague-Dawley rats of about 6 weeks old received subcutaneous administration at the following dosage: 38 µg/kg for the FSH-Fc/Fc heterodimeric protein; 3.8 µg/kg (equivalent to 50 IU/kg) for the control Gonal-F. Blood was collected postorbitally at 0, 2, 4, 8, 12, 24, 48, 72, 96, 144, and 192 hours after administration, with a collection volume of 100 µL each time, and the serum obtained after centrifugation was frozen at –80° C. for ELISA analysis. A sandwich ELISA assay was conducted with an anti-FSH coating antibody (Fitzgerald Industries, Catalog No. 10-F20A) and a horseradish peroxidase-coupled anti-Fc detection antibody (Lakepharma, Catalog No. 203150), and the results are shown in FIG. 11. Comparing to the control Gonal-F, the FSH-Fc/Fc heterodimeric protein peaked more slowly and had a longer half-life. The FSH-Fc/Fc heterodimeric protein had an in vivo half-life of about 84 hours and a $T_{max}$ of about 48 hours in rats; while Gonal-F had a half-life of about 7 hours and a $T_{max}$ of about 5 hours. The results suggested that the in vivo half-life of the FSH-Fc/Fc heterodimer in rats was more than 10 times longer than that of Gonal-F. In view of the results of the preliminary pharmacokinetic assay for the FSH-Fc/Fc heterodimer in Example 4 (the in vivo half-life of the FSH-Fc/Fc heterodimer was about 6-8 times longer than that of Gonal-F in rats), this indicates that the FSH-Fc/Fc heterodimer thus isolated and purified had a significantly increased in vivo half-life in rats.

EXAMPLE 9.

In vivo Pharmacokinetic Study for FSH-Fc/Fc Heterodimer in Cynomolgus Monkeys

Figure 12:
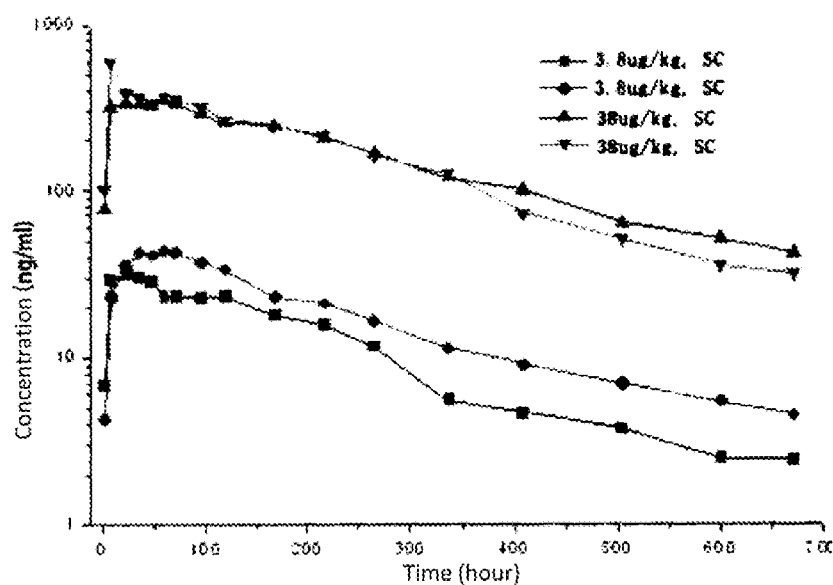
FIG. 12 is graph showing the concentration-time curves of serum FSH-Fc/Fc from cynomolgus monkeys after (A) a single subcutaneous dose of 3.8 and 38 μg/kg of the FSH-Fc/Fc heterodimer and (B) a single intravenous dose of 38 μg/kg of the FSH-Fc/Fc heterodimer. Each curve corresponds to a monkey.
Figure 12:
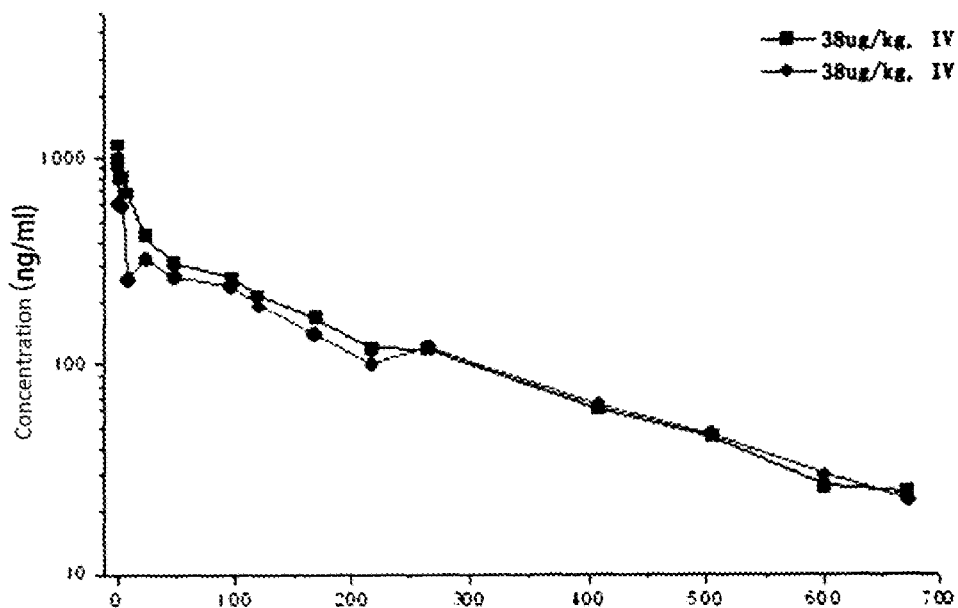

An in vivo pharmacokinetic study was conducted for the purified FSH-Fc/Fc heterodimer isolated and prepared in Example 6 in cynomolgus monkeys. The specific protocol is as follows: female cynomolgus monkeys of 3-4 years old received administration via the following two routes: subcutaneous and intravenous injection; the dosage for subcutaneous administration: 3.8 µg/kg and 38 µg/kg of the FSH-Fc/Fc heterodimeric protein; the dosage for intravenous injection: 38 µg/kg. Blood was collected postorbitally at 0, 2, 8, 24, 36, 48, 60, 72, 96, 120, 168, 216, 264, 336, 408, 504, 600, and 672 hours after subcutaneous administration, with a collection volume of 100 µL each time, and the serum obtained after centrifugation was frozen at –80° C. for ELISA analysis. Blood was collected at 0.25, 1, 4, 8, 24, 48, 96, 120, 168, 216, 264, 336, 408, 504, 600, and 672 hours after intravenous administration, and treated according to the method for ELISA analysis described above. A sandwich ELISA assay was conducted with an anti-FSH coating antibody (Fitzgerald Industries, Catalog No. 10-F20A) and a horseradish peroxidase-coupled anti-Fc detection antibody (Lakepharma, Catalog No. 203150), and the results are shown in FIG. 12. Key pharmacokinetic parameters were calculated by the non-compartment model (NCA) using WinNonlin (V6.2), and the results showed that the FSH-Fc/Fc heterodimeric protein had a half-life of more than 200 h in cynomolgus monkeys when administered through subcutaneous injection; the drug was sufficiently absorbed, and the average absolute bioavailability (the area under the curve for subcutaneous administration from 0 to 672 h/the area under the curve for intravenous administration from 0 to 672 h (%)) was close to 100%, when the drug was injected subcutaneously at 38 µg/kg; since the drug was absorbed relatively rapidly and fully, no sudden drop in the plasma drug concentration was seen within 28 days after administration, suggesting that no antibody against the drug was produced within 28 days after a single dose subcutaneous injection; when the drug was injected subcutaneously (3.8-38 µg/kg), the amount of plasma drug exposure was positively correlated with the dosage, substantially complying with the linear kinetic characteristics.

EXAMPLE 10.

Figure 13:
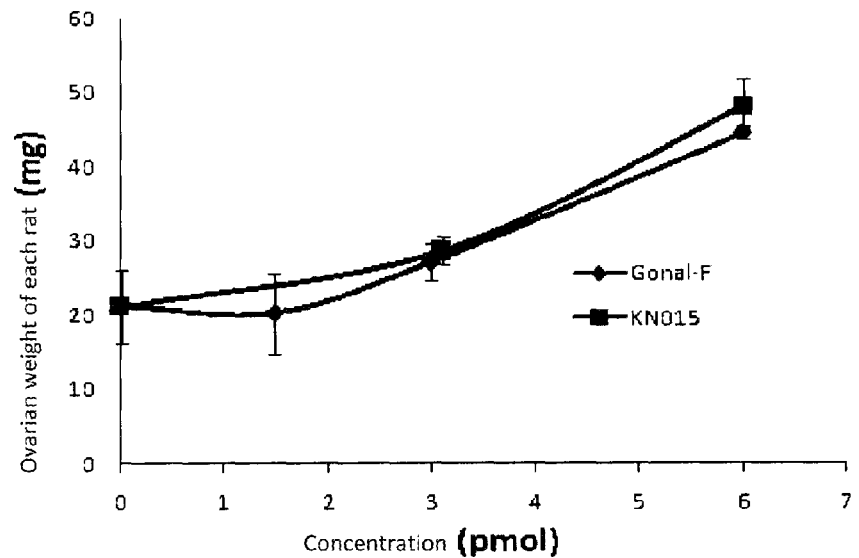
FIG. 13 is a graph showing the ovarian weight-dosage curves of 21-day-old female SD rats receiving a single subcutaneous dose of the FSH-Fc/Fc heterodimer and receiving the Gonal-F twice a day. The ovaries were weighed 72 hours after administration.

In vivo Pharmacodynamic Study for FSH-Fc/Fc Heterodimer: Ovary Weighing Assay in Rats An ovary weighing assay was conducted for the purified FSH-Fc/Fc heterodimer isolated and prepared in Example 6 in rats. Healthy, qualified female Sprague-Dawley rats of about 21 days old were selected. The dosages for the sample and the control Gonal-F were 0, 3, 6, and 12 pmol (equivalent to 0, 1.25, 2.5, and 5 IU for Gonal-F), respectively; the sample was only administered subcutaneously once, while the control Gonal-F was administered twice a day. The ovaries were weighed after 72 hours, and the results are shown in FIG. 13. Comparing to the control Gonal-F, within the dosage range of 0-6 pmol (equivalent to 0-2.5 IU for Gonal-F), the same molar of sample lead to comparable increases in ovarian weight; and the dosage of the FSH-Fc/Fc heterodimer is positively correlated with the increase in ovarian weight.

EXAMPLE 11.

Figure 14:
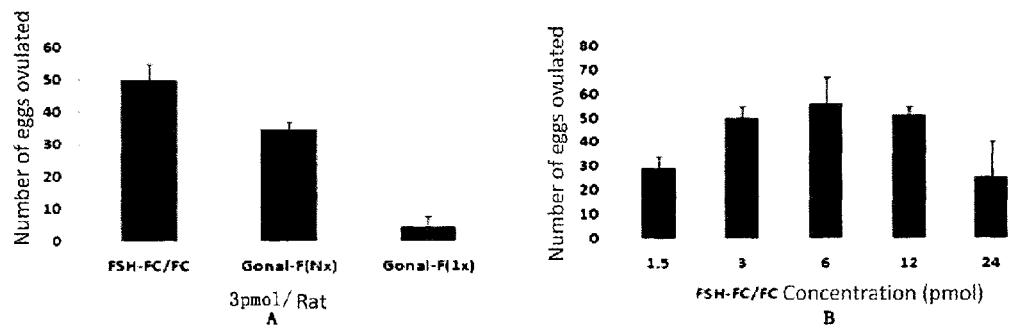
FIG. 14(A) is a histogram showing the number of oocytes in 26-day-old female SD rats receiving a single subcutaneous dose at a dosage of 3 pmol of the FSH-Fc/Fc heterodimer, and of the Gonal-F twice a day (N×) and once (1×) a day; (B) is a histogram showing the number of oocytes vs. dosage in 26-day-old female SD rats receiving a single subcutaneous dose of the FSH-Fc/Fc heterodimer. hCG was injected 72 hours after administration, and 24 hours later, follicles were counted.

In vivo Pharmacodynamic Study for FSH-Fc/Fc Heterodimer: Ovulation Assay in Rats A study of ovulation assay was conducted for the purified FSH-Fc/Fc heterodimer isolated and prepared in Example 6 in rats, the relationship between different dosages of the FSH-Fc/Fc heterodimer and the effect on ovulation was investigated, the effects on ovulation were also compared between the same molar dosage of FSH-Fc/Fc heterodimer and the control Gonal-F. The specific protocol is as follows: healthy, qualified female Sprague-Dawley rats of about 26-28 days old were selected. The sample was administered subcutaneously at a dosage of 3, 6, 12, or 24 pmol only once;

while the control Gonal-F was administered at a dosage of 3 pmol (equivalent to 1.25 IU) twice a day (N×) or only once (1×). 13.3 IU hCG (human chorionic gonadotropin) was administered after 72 hours. The rats were sacrificed 24 hours after hCG administration, and the oocytes were counted. The results are summarized in FIG. 14. When the dosage was 3 pmol, the number of oocytes produced upon stimulation by administration of the FSH-Fc/Fc heterodimer only once was even more than that produced upon stimulation by administration of Gonal-F twice a day. The number of oocytes produced upon stimulation with the FSH-Fc/Fc heterodimer was dosage-dependent to some extent. When the dosage is within 6 pmol, the dosage of the FSH-Fc/Fc heterodimer was positively correlated with the number of oocytes, and the number of egg cells reached a plateau at a dosage of 6 pmol, and subsequently decreased with an increase of the dosage.

While specific embodiments of the present disclosure have been shown and described in detail, those skilled in the art will appreciate that numerous modifications and substitutions can be made to those details according to the overall teachings disclosed herein, and all of these changes fall within the scope of the present invention. It is intended that the scope of the present invention is defined by the appended claims and any equivalents thereto.

What is claimed is:

1. A fusion protein comprising a trophic hormone protein having an α-subunit, a β-subunit and an Fc fragment of an antibody, wherein the β-subunit of the trophic hormone protein is linked to the Fc fragment directly or indirectly via a linker, and the α-subunit of the trophic hormone protein binds to the β-subunit via intermolecular interactions between the α-subunit and the β-subunit, wherein the α-subunit of the trophic hormone is not directly or indirectly linked to an Fc fragment, and wherein the trophic hormone is selected from the group consisting of luteotropic hormone, follicle stimulating hormone, chorionic gonadotropin, and thyroid stimulating hormone.

2. A heterodimeric protein comprising one fusion protein according to claim 1 and an Fc chain, wherein the Fc chain is associated with the Fc fragment in the fusion protein via chemical association.

3. The heterodimeric protein according to claim 2, wherein the heterodimeric protein has the formula:

αFSH@βFSH-L-Fc:Fc, wherein "FSH" refers to follicle stimulating hormone protein,
"α" refers to the α-subunit of the follicle stimulating hormone protein,
"β" refers to the β-subunit of the follicle stimulating hormone protein,
"@" is the intermolecular interaction between the α-subunit and β-subunit of the follicle stimulating hormone protein,
"L" represents direct linking between the β-subunit and Fc fragment or indirect linking via a linker,
"Fc" refers to the Fc fragment of an immunoglobulin, and
":" refers to the chemical association between βFSH-L-Fc and Fc.

4. The heterodimeric protein according to claim 2, wherein the heterodimeric protein has the formula:

Ta-αXXX@βXXX-L-Fc:Fc or Ta-Fc:Fc-L-βXXX@αXXX wherein "XXX" refers to follicle stimulating hormone,
"α" refers to the α-subunit of the follicle stimulating hormone,
"β" refers to the β-subunit of the follicle stimulating hormone,
"@" is the intermolecular interaction between the α-subunit and β-subunit of the trophic hormone protein,
"L" represents direct linking between the β-subunit and Fc fragment or indirect linking via a linker,
"Fc" refers to the Fc fragment of an immunoglobulin,
":" refers to the chemical association between βXXX-L-Fc and Fc, and
"Ta" refers to a protein purification tag.

5. A pharmaceutical composition comprising the fusion protein according to claim 1, and a pharmaceutically acceptable carrier or excipient.

6. A recombinant expression vector comprising a nucleotide sequence encoding an α-subunit of a trophic hormone protein, a nucleotide sequence encoding a fusion protein comprising a β-subunit of the trophic hormone protein and an Fc fragment of an antibody, and a nucleotide sequence encoding an Fc fragment of an antibody, wherein each of the proteins is transcribed and translated independently, and the trophic hormone is selected from the group consisting of luteotropic hormone, follicle stimulating hormone, chorionic gonadotropin and thyroid stimulating hormone.

7. A recombinant cell comprising the recombinant expression vector according to claim 6.

8. A method for preparing a heterodimeric protein comprising a fusion protein that comprises a trophic hormone protein having an α-subunit and a β-subunit and an Fc fragment of an antibody, wherein the β-subunit of the trophic hormone protein is linked to the Fc fragment directly or indirectly via a linker, and the α-subunit of the trophic hormone protein binds to the β-subunit via intermolecular interactions between the α-subunit and the β-subunit, wherein the α-subunit of the trophic hormone is not directly or indirectly linked to an Fc fragment, and wherein the trophic hormone is selected from the group consisting of luteotropic hormone, follicle stimulating hormone, chorionic gonadotropin and thyroid stimulating hormone, and an Fc chain, wherein the Fc chain is associated with the Fc fragment in the fusion protein via chemical association, comprising the step of isolating and purifying a mixture of heterodimeric proteins and homodimeric proteins, wherein the homodimeric proteins comprise two fusion proteins, wherein each fusion protein comprises a trophic hormone protein having an α-subunit and a β-subunit and an Fc fragment of an antibody, wherein the β-subunit of the trophic hormone protein is linked to the Fc fragment directly or indirectly via a linker, and the α-subunit of the trophic hormone protein binds to the β-subunit via intermolecular interactions between the α-subunit and the β-subunit, wherein the α-subunit of the trophic hormone is not directly or indirectly linked to an Fc fragment, and wherein the trophic hormone is selected from the group consisting of luteotropic hormone, follicle stimulating hormone, chorionic gonadotropin and thyroid stimulating hormone, and wherein the Fc fragments in the two fusion proteins are associated with each other via chemical association to obtain the heterdimeric protein.

9. The fusion protein according to claim 1, wherein the trophic hormone is follicle stimulating hormone.

10. The fusion protein according to claim 9, wherein the follicle stimulating hormone α-subunit comprises a sequence according to SEQ ID NO: 1.

11. The fusion protein according to claim 9, wherein the follicle stimulating hormone β-subunit linked to the Fc fragment comprises a sequence according to SEQ ID NO:4.

12. The fusion protein according to claim 9, wherein the follicle stimulating hormone α-subunit comprises a sequence according to SEQ ID NO:1 and the follicle stimulating hormone β-subunit linked to the Fc fragment comprises a sequence according to SEQ ID NO:4.

13. The fusion protein according to claim 1, wherein the Fc fragment comprises a hinge region, a CH2 domain, and a CH3 domain of an immunoglobulin.

14. The fusion protein according to claim 1, wherein the Fc fragment comprises an IgG1 Fc.a.

* * * * *